US010497116B2

(12) United States Patent
Chen et al.

(10) Patent No.: US 10,497,116 B2
(45) Date of Patent: Dec. 3, 2019

(54) CYTOLOGICAL IMAGE PROCESSING DEVICE, AND METHOD FOR QUANTIFYING CHARACTERISTICS OF CYTOLOGICAL IMAGE

(71) Applicant: AMCAD BIOMED CORPORATION, Taipei (TW)

(72) Inventors: Argon Chen, Taipei (TW); Yi-Hsien Hsiao, Taipei (TW); Tien-Chun Chang, Taipei (TW); I-Shiow Jan, Taipei (TW); Shyang-Rong Shih, Taipei (TW); Hsuan-Mao Wang, Taipei (TW)

(73) Assignee: AMCAD BIOMED CORPORATION, Taipei (TW)

( * ) Notice: Subject to any disclaimer, the term of this patent is extended or adjusted under 35 U.S.C. 154(b) by 142 days.

(21) Appl. No.: 15/808,589

(22) Filed: Nov. 9, 2017

(65) Prior Publication Data

US 2018/0130205 A1 May 10, 2018

Related U.S. Application Data

(60) Provisional application No. 62/419,928, filed on Nov. 9, 2016.

(51) Int. Cl.
*G06T 7/00* (2017.01)
*G06T 7/11* (2017.01)
(Continued)

(52) U.S. Cl.
CPC ............. *G06T 7/0012* (2013.01); *G01N 1/30* (2013.01); *G02B 21/06* (2013.01); *G06K 9/0014* (2013.01);
(Continued)

(58) Field of Classification Search
CPC ......... G06T 7/0012; G06T 7/181; G06T 7/11; G06T 7/194; G06T 7/73; G06T 7/136;
(Continued)

(56) References Cited

U.S. PATENT DOCUMENTS

2010/0183216 A1* 7/2010 Yamada ............. G01N 15/1475
382/134
2015/0078648 A1 3/2015 Lee et al.
2017/0178361 A1* 6/2017 Berezhna .............. G06T 7/0014

FOREIGN PATENT DOCUMENTS

CN 105139383 A 12/2015
TW 201510936 A 3/2015

OTHER PUBLICATIONS

EPO, Extended Search Report dated Jul. 4, 2018 in European Patent Application No. 17194325.1, 16 pages.
(Continued)

*Primary Examiner* — Jon Chang
(74) *Attorney, Agent, or Firm* — Masuvalley & Partners

(57) ABSTRACT

A cytological image processing device, a method for quantifying characteristics of cytological image and a non-transitory computer readable medium thereof are provided. The cytological image processing device executes the method including the steps: loading a cytological image with a plurality of pixels; removing a background part from the cytological image according to at least one of a plurality of color attributes of each pixel of the cytological image in a color space to obtain a background-subtracted image; dividing the background-subtracted image into a nuclear part and a cytoplasmic part; detecting a plurality of edge pixels in the background-subtracted image to segment a plurality of nuclear blocks in the background-subtracted image; generating a parameter set according to the nuclear blocks; and generating an output image by visualizing the background-subtracted image.

15 Claims, 18 Drawing Sheets

(51) Int. Cl.
| | |
|---|---|
| *G06T 7/194* | (2017.01) |
| *G06K 9/00* | (2006.01) |
| *G06K 9/46* | (2006.01) |
| *G06T 7/136* | (2017.01) |
| *G06T 7/12* | (2017.01) |
| *G01N 1/30* | (2006.01) |
| *G06K 9/62* | (2006.01) |
| *G06T 7/90* | (2017.01) |
| *G02B 21/36* | (2006.01) |
| *G06T 7/181* | (2017.01) |
| *G06T 7/73* | (2017.01) |
| *G02B 21/06* | (2006.01) |

(52) U.S. Cl.
CPC ....... *G06K 9/00127* (2013.01); *G06K 9/4604* (2013.01); *G06K 9/6202* (2013.01); *G06K 9/6232* (2013.01); *G06T 7/0008* (2013.01); *G06T 7/11* (2017.01); *G06T 7/12* (2017.01); *G06T 7/136* (2017.01); *G06T 7/181* (2017.01); *G06T 7/194* (2017.01); *G06T 7/73* (2017.01); *G02B 21/365* (2013.01); *G06T 7/90* (2017.01); *G06T 2207/10056* (2013.01); *G06T 2207/20132* (2013.01); *G06T 2207/30024* (2013.01)

(58) Field of Classification Search
CPC ............... G06T 7/12; G06T 7/0008; G06T 2207/10024; G06T 2207/10056; G06T 2207/30024; G06T 2207/20132; G06T 7/90; G06K 9/00127; G06K 9/0014; G06K 9/6232; G06K 9/6202; G06K 9/4604; G01N 1/30; G02B 21/06; G02B 21/365
See application file for complete search history.

(56) References Cited

OTHER PUBLICATIONS

William A Christens-Barry et al, "Quantitative Grading of Tissue and Nuclei in Prostate Cancer for Prognosis Prediction" Johns Hopkins APL Technical Digest, vol. 18, No. 2 (1997), p. 226-233.
Tomasz Les et al, "Fusion of Fish image analysis methods of HER2 status determination in breast cancer", Expert Systems With Applications, Oxford GB, vol. 61, May 13, 2016, p. 78-85.
Monica K. Chawla et al., "3D-catFICH: a system for automated quantitative three-dimensional compartmental analysis of temporal gene transcription activity imaged by fluorescence in situ hybridization", Journal of Neuroscience Methods, Elsevier Science Publisher B.V., Amsterdam, NL, vol. 139, No. 1, Oct. 15, 2004, p. 13-24.
Wei Xiong et al., "Cell Clumping Quantification and Automatic Area Classification in Peripheral Blood Smear Images", 2009 2nd International Conference on Biomedical Engineering and Informatics, BMEI 2009, Tianjin, China, Oct. 17-19, 2009, pp. 1-5.
European Patent Office(EPO), European Search Report dated Mar. 22, 2018, in European Patent Application No. 17194325.1, 14 pages.
Taiwan Intellectual Property Office(TIPO), First Notification of Office Action dated Mar. 15, 2018 in Taiwan Patent Application No. 106137944, 11 pages with an English translation.
Herbert Ramoser et al, "Leukocyte segmentation and classification in blood-smear images", Proceedings of the 2005 IEEE, Engineering in Medicine and Biology 27th Annual Conference, Sep. 1-4, 2005, pp. 3371-3374 Shanghai, China, total 4 pages.
Omid Sarrafzadeh et al, "A Simple and Accurate Mtthod for White Blood Cells Segmentation Using K-Means Algorithm", 2015, IEEE, total 6 pages.
Congcong Zhang et al., "White Blood Cell Segmentation by Color-Space-Based K-Means Clustering", Sensors 2014, published on Sep. 1, 2014, pp. 16128-16147, total 20 pages.
Vassili A. Kovalev et al., "Robust Recognition of White Blood Cell Images", 1996, IEEE, pp. 371-375, total 5 pages.
P.R. Tabrizi et al., "Using PCA and LVQ Neural Network for Automatic Recognition of Five Types of Whit Blood Cells" on Aug. 31-Sep. 4, 2010 in Buenos Aires, Argentina, 2010 IEEE, pp. 5593-5596, total 4 pages.

* cited by examiner

Connecting the edge pixels according to a 8-connection connectivity rule to form a plurality of line segments, wherein the total gradient magnitude of a next edge pixel connected to a current edge pixel is greater than a first threshold and an angle between a total gradient direction of of the current edge pixel and a total gradient direction of the next edge pixel connected to the current edge pixel is less than a second threshold — S401

FIG. 4A

Connecting the edge pixels according to the 8-connection connectivity rule to form a plurality of line segments, wherein an angle between the total gradient direction of the current edge pixel and the total gradient direction of the next edge pixel connected to the current edge pixel is less than a second threshold ⸺ S601

FIG. 6A

CYTOLOGICAL IMAGE PROCESSING DEVICE, AND METHOD FOR QUANTIFYING CHARACTERISTICS OF CYTOLOGICAL IMAGE

This application claims the benefit of and is a non-provisional of co-pending U.S. Provisional Application Ser. No. 62/419,928 filed on Nov. 9, 2016, which is hereby expressly incorporated by reference in its entirety for all purposes.

CROSS-REFERENCES TO RELATED APPLICATIONS

Not applicable.

BACKGROUND OF THE INVENTION

Field of the Invention

The present invention relates to a cytological image processing device, and a method for quantifying characteristics of cytological image. More particularly, the cytological image processing device of the present invention executes the method for quantifying characteristics of cytological image to obtain nuclear blocks in a cytological image, and outputs a parameter set and a visualized image according to the nuclear blocks.

Descriptions of the Related Art

With the rapid development of the science and technology, technologies for digitalizing data and images have gradually been mature. Electronic products (e.g., computers, tablet computers, and smart phones), therefore, become the most important requisite of all walks of life to store data and present images.

Conventional clinical cytological examination uses a light microscope to observe a stained slide carrying cells of a patient so as to generate a cytological image. Thereafter, a doctor can make a diagnosis according to the distribution of the nucleus and the cytoplasm on the cytological image of the patient to determine possible diseases. However, in the case where the diagnosis is made only depending on the cytological image without performing advanced processing on the cytological image to obtain relevant quantified parameters or analyzed images, different doctors may give quite different diagnosis results for the same cytological image, and the excessively subjective diagnosis results will influence the accuracy of diagnosis when determining the illness condition of the patient.

Accordingly, an urgent need exists in the art to perform advanced processing on the cytological image to obtain relevant quantified parameters or analyzed images, thereby providing the doctor with advanced information about the cytological image to assist the doctor in making the diagnosis, reducing the disagreement among the diagnosis results made by different doctors for the same cytological image, and improving the accuracy of diagnosis when determining the illness condition of the patient.

SUMMARY OF THE INVENTION

An objective of the present invention is to provide relevant quantified parameters and analyzed images of the cytological image. The present invention may divide the cytological image into a nuclear part and a cytoplasmic part and segment nuclear blocks representing the nuclei, thereby generating relevant quantified parameters of the cytological image and providing an output image to visualize the nuclear blocks. In this way, as compared to the prior art, the present invention can provide the doctor with advanced information about the cytological image to assist the doctor in making the diagnosis, and reduce the disagreement among the diagnosis results made by different doctors for the same cytological image, thereby improving the accuracy of diagnosis when determining the illness condition of the patient.

To achieve the aforesaid objective, the present invention discloses a method for quantifying characteristics of cytological image that is used in a cytological image processing device. The method for quantifying characteristics of cytological image comprises the following steps of: (a) loading a cytological image having a plurality of pixels; (b) removing a background part from the cytological image according to at least one of a plurality of color attributes of each of the pixels in a color space to obtain a background-subtracted image; (c) dividing the background-subtracted image into a nuclear part and a cytoplasmic part; and (d) generating a nuclei-to-cytoplasm color ratio according to the nuclear part and a cytoplasmic part.

Moreover, the present invention further discloses a method for quantifying characteristics of cytological image that is used in a cytological image processing device. The method for quantifying characteristics of cytological image comprises the following steps of: (a) loading a cytological image having a plurality of pixels; (b) removing a background part from the cytological image according to at least one of a plurality of color attributes of each of the pixels in a color space to obtain a background-subtracted image; (c) dividing the background-subtracted image into a nuclear part and a cytoplasmic part; (d) detecting a plurality of edge pixels in the background-subtracted image to segment a plurality of nuclear blocks in the background-subtracted image; (e) generating a parameter set, the parameter set including at least one of the following: a nuclear polarity, an index of intranuclear cytoplasmic pseudoinclusions and an index of nuclear overlapping and molding, wherein the nuclear polarity is generated according to the nuclear blocks, the index of intranuclear cytoplasmic pseudoinclusions is generated according to the nuclear part, and the index of nuclear overlapping and molding is generated according to the nuclear blocks and the nuclear part; and (f) generating an output image by visualizing the background-subtracted image.

Moreover, the present invention further discloses a cytological image processing device which comprises a storage and a processor. The processor is electrically connected to the storage. The processor executes the method for quantifying characteristics of cytological image, and the method comprises the following steps: (a) loading a cytological image having a plurality of pixels from the storage; (b) removing a background part from the cytological image according to at least one of a plurality of color attributes of each of the pixels in a color space to obtain a background-subtracted image; (c) dividing the background-subtracted image into a nuclear part and a cytoplasmic part; (d) detecting a plurality of edge pixels in the background-subtracted image to segment a plurality of nuclear blocks in the background-subtracted image; (e) generating a parameter set, the parameter set including at least one of the following: a nuclear polarity, an index of intranuclear cytoplasmic pseudoinclusions, a nuclei-to-cytoplasm color ratio and an index of nuclear overlapping and molding, wherein nuclei-to-cytoplasm color ratio is generated according to the nuclear part and the cytoplasmic part, the nuclear polarity is generated according to the nuclear blocks, the index of intranuclear cytoplasmic pseudoinclusions is generated according to the nuclear part, and the index of nuclear overlapping and molding is generated according to the nuclear blocks and the nuclear part; and (f) generating an output image by visualizing the background-subtracted image.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

FIG. 3, FIG. 4A, FIG. 4B and FIG. 4C illustrate flowcharts of the method in the edge detection stage according to a second embodiment of the present invention;

FIG. 5, FIG. 6A, FIG. 6B and FIG. 6C illustrate flowcharts of the method in the edge detection stage according to a fourth embodiment of the present invention;

DESCRIPTION OF THE PREFERRED EMBODIMENT

In the following description, the present invention will be explained with reference to embodiments thereof. However, these embodiments of the present invention are not intended to limit the present invention to any environment, applications or implementations described in these embodiments. Therefore, description of these embodiments is only for purpose of illustration rather than to limit the scope of the present invention. It shall be appreciated that, in the following embodiments and the attached drawings, elements unrelated to the present invention are omitted from depiction.

Figure 1:
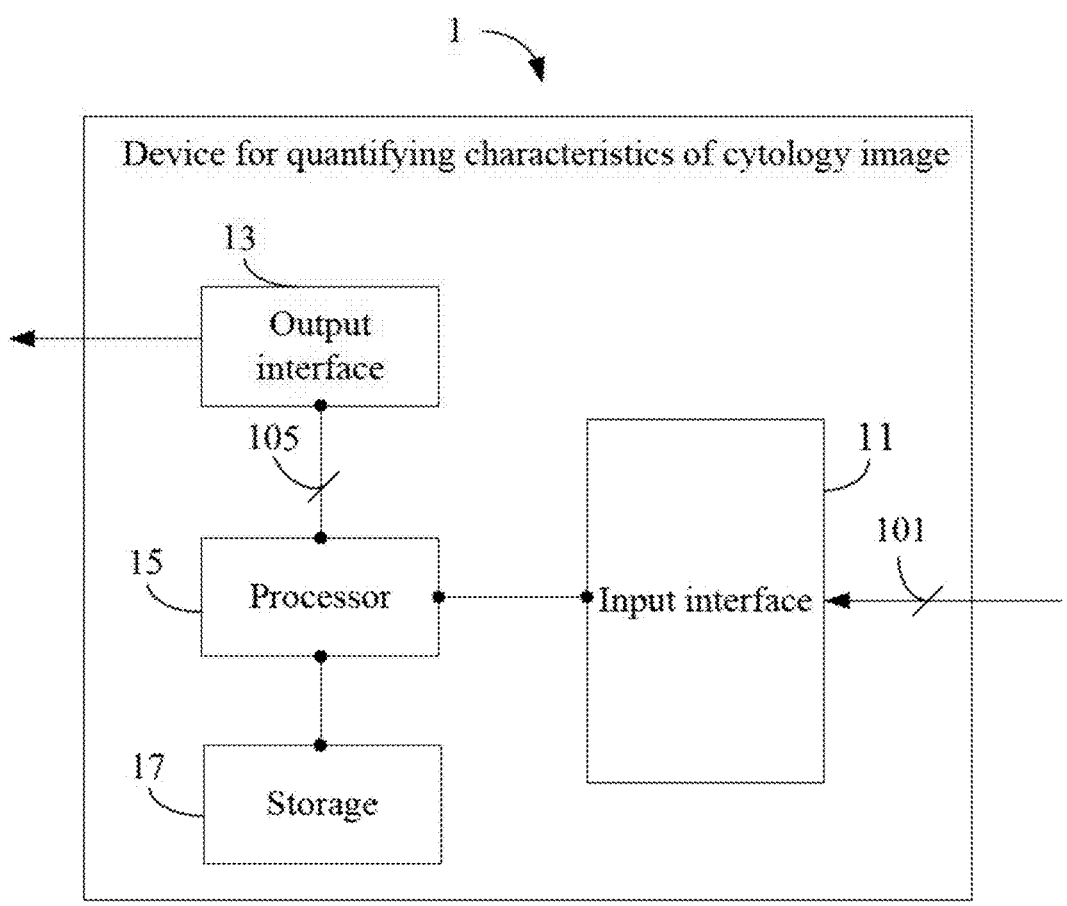
FIG. 1 is a schematic view depicting a device 1 for quantifying characteristics of cytological image according to a first embodiment of the present invention.
Figure 2A:
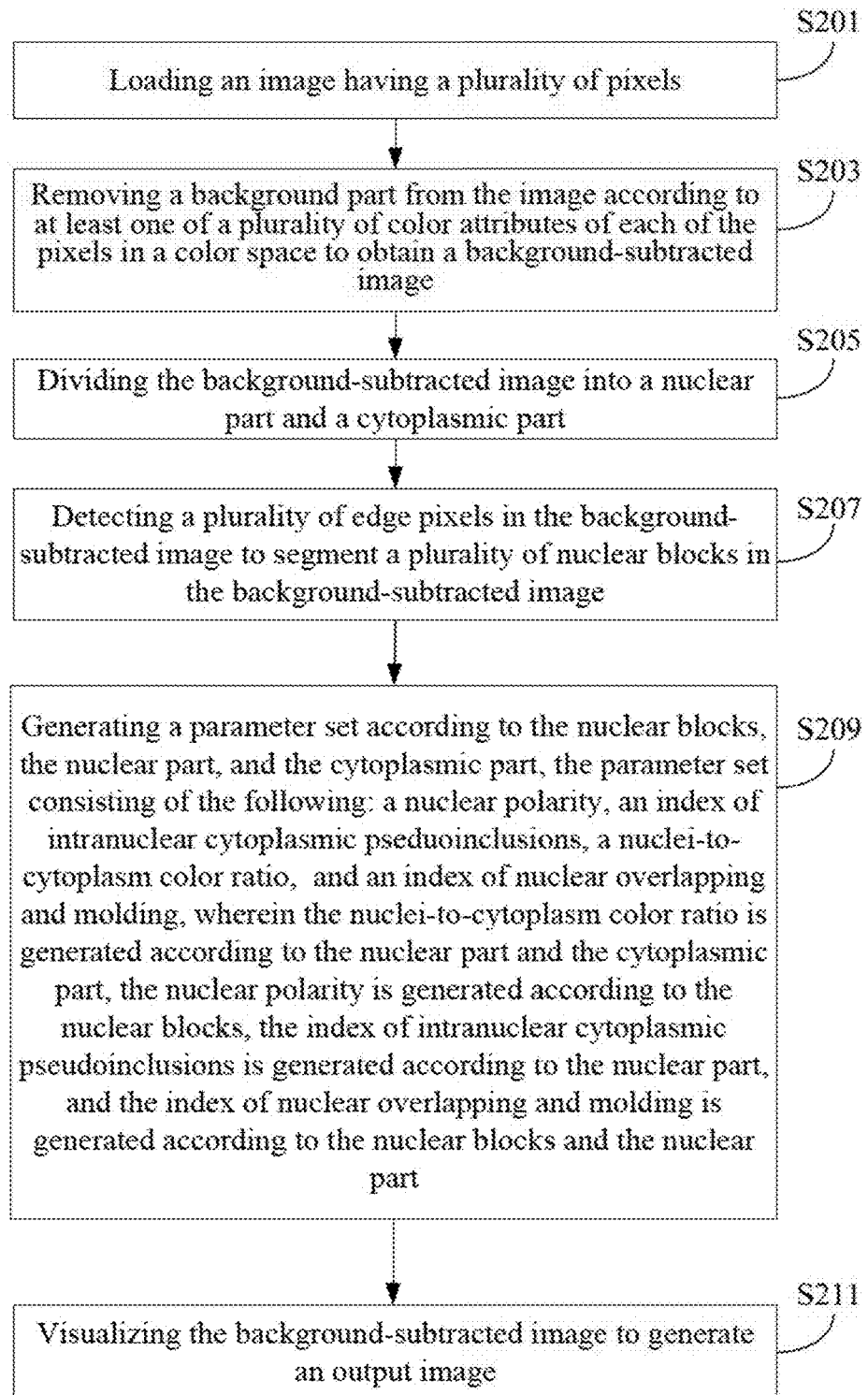
FIG. 2A is a flowchart diagram depicting a method for quantifying characteristics of cytological image according to the first embodiment of the present invention.

A first embodiment of the present invention is as shown in FIG. 1 and FIG. 2A. FIG. 1 is a schematic view of a cytological image processing device 1 according to the present invention. The cytological image processing device 1 comprises an input interface 11, an output interface 13, a processor 15 and a storage 17. The processor 15 is electrically connected to the input interface 11, the output interface 13 and the storage 17.

Figure 7A:
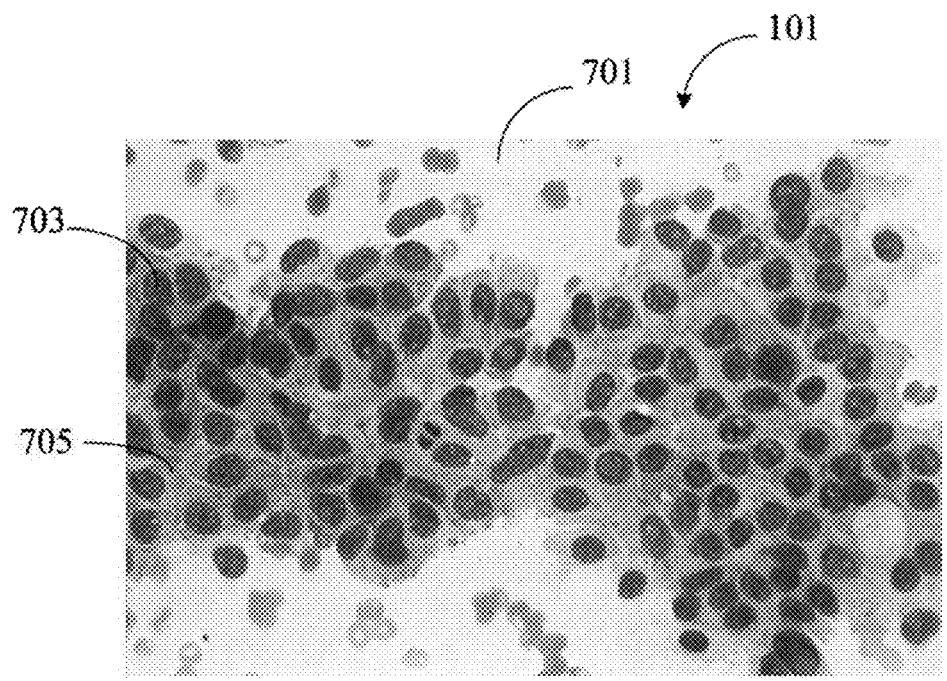
FIG. 7A depicts a cytological image.

The input interface 11 is used to receive a cytological image 101 which has been stained (e.g., a cytological image with a magnification factor of 400×, as shown in FIG. 7A, including a background part 701, nuclei 703, and cytoplasm 705) generated by a light microscope (or any image sensor having a high magnification factor). The input interface 11 may be a wired interface (e.g., a USB transmission interface, but not limited thereto) or a wireless transmission interface (e.g., a WIFI transmission interface), and it may be connected to the light microscope or connected to a storage device storing the cytological image. The processor 15 receives the cytological image 101 via the input interface 11 and stores the cytological image 101 into the storage 17. The output interface 13 may be a data transmission interface or an image transmission interface, and it is used to output relevant quantified parameters of the cytological image and the visualized image of nuclei generated by the processor 15.

The processor 15 is configured to execute the method for quantifying characteristics of cytological image according to the present invention, thereby generating relevant quantified parameters of the cytological image and the visualized image. The method for quantifying characteristics of cytological image according to the present invention may be implemented by a non-transitory computer readable medium. The non-transitory computer readable medium stores a computer program comprising a plurality of codes. When the computer program is loaded and installed into an electronic device (e.g., the cytological image processing device 1), the codes comprised in the computer program are executed by the processor of the electronic device to execute the method for quantifying characteristics of cytological image according to the present invention. The non-transitory computer readable medium may be for example a read only memory (ROM), a flash memory, a floppy disk, a hard disk, a compact disk (CD), a mobile disk, a magnetic tape, a database accessible to networks, or any other storage media with the same function and well known to those skilled in the art.

A flowchart of a method for quantifying characteristics of cytological image according to the present invention is as shown in FIG. 2A. First, in step S201, the processor 15 loads a cytological image 101 from the storage 17. The cytological image 101 comprises a plurality of pixels to present a plurality of cells at a certain magnification factor. The position of each of the pixels in the cytological image 101 is represented by a x value in a horizontal direction and a y value in a vertical direction, so the pixels in the cytological image 101 form a two-dimensional (2D) matrix.

It shall be appreciated that, the cytological image 101 may be represented by RGB (red, green, and blue) color space, HSV (hue, saturation, and value) color space or any color space, and it may be flexibly converted from any color space to another color space. For example, if the loaded cytological image 101 is represented by the RGB color space, then the processor 15 may convert the cytological image 101 from being represented by the RGB color space to being represented by the HSV color space. Since the conversion mechanism of the color space is well known in the art, this will not be further described herein.

Figure 7B:
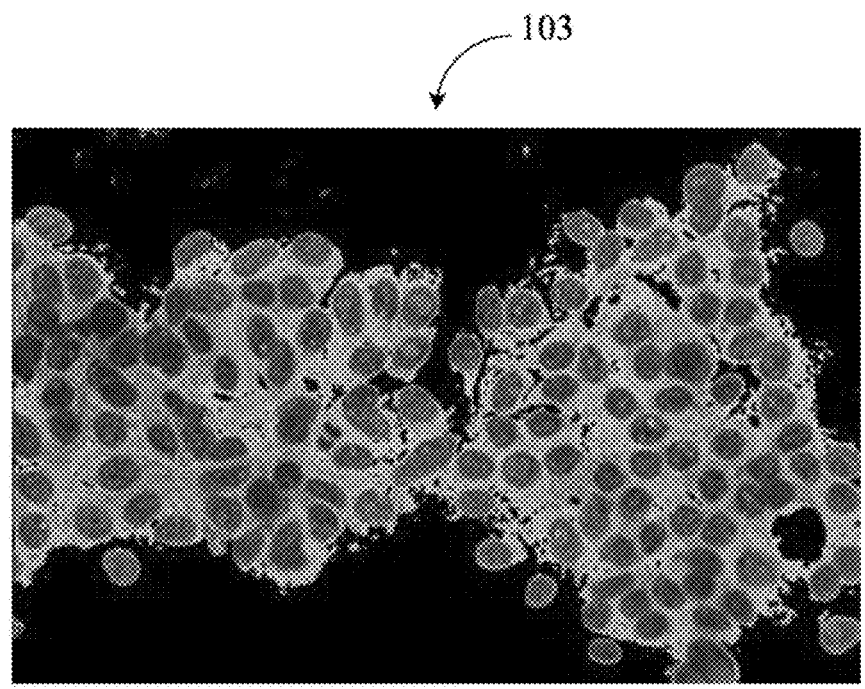
FIG. 7B depicts a background-subtracted image.

Then, in step S203, the processor 15 divides the pixels of the cytological image 101 into a cell part and a background part and removes the background part from the cytological image 101 to obtain a background-subtracted image 103 according to at least one of a plurality of color attributes of the pixels of the cytological image 101 in a color space, as shown in FIG. 7B (i.e., removing the background part 701 in FIG. 7A). It shall be appreciated that, the background part 701 herein refers to the unstained part in the image after the cytological image 101 is stained (it is usually the region excluding cells).

Figure 12:
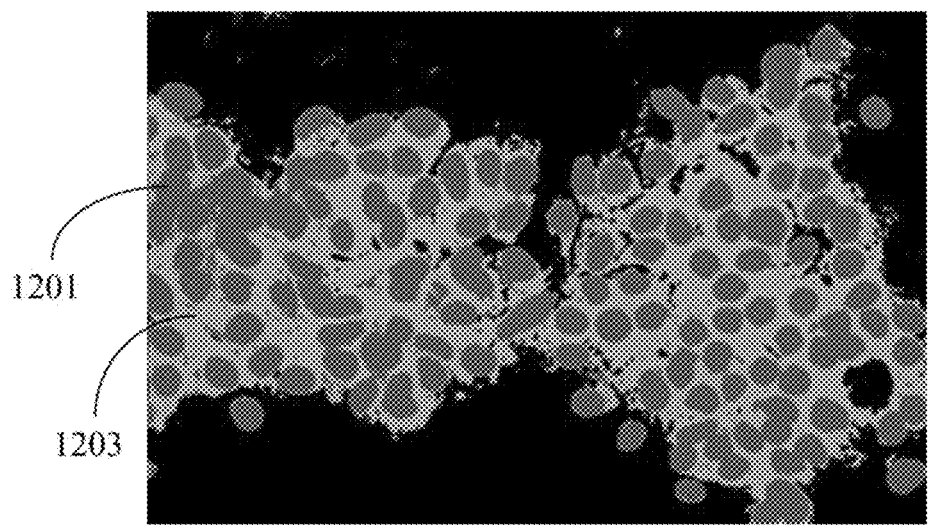
FIG. 12 depicts the visualization of a nuclei-to-cytoplasm ratio (NCR)

Thereafter, in step S205, the processor 15 divides the pixels in the background-subtracted image 103 into a nuclear part 1201 and a cytoplasmic part 1203, as shown in FIG. 12. It shall be appreciated that, a clustering algorithm may be adopted to divide the pixels of the cytological image 101 and to divide the pixels of the background-subtracted image 103. One-dimensional, two-dimensional or three-dimensional clustering, or even multi-round clustering may be performed respectively with respect to one, two or three specific attributes (i.e., color attributes) of each pixel in a certain proportion. Moreover, the clustering algorithm adopted in the present invention may be the K-means clustering, but it is not limited thereto. Therefore, any clustering algorithm achieving the same purpose shall fall within the scope of the present invention.

For example, when the color space is the HSV color space (i.e., formed by three attributes, namely, hue, saturation and value), the processor 15 may perform three rounds of K-means clustering with respect to at least one of the three attributes (i.e., hue, saturation and value). The first two rounds of clustering aim at removing the background part, while the third round of clustering aims at distinguishing the cytoplasmic part from the nuclear part.

In detail, in the first round of K-means clustering, the hue is adopted as the standard, and a difference between a maximum value and a minimum value of the hue of the pixels is divided into six equal parts to determine six initial reference points. If the maximum value of the hue of the pixels is 80 and the minimum value thereof is 30, then the hue of the six initial reference points is respectively 30, 40, 50, 60, 70 and 80. Accordingly, the pixels of the cytological image 101 may be divided into six groups by performing one-dimensional K-means clustering on the pixels according to the six initial reference points, and the pixels are divided into a cell part and a background part according to the six groups. In this way, the processor 15 can remove the pixels classified as the background part to generate the background-subtracted image 103.

Next, the second round of K-means clustering is performed on the background-subtracted image 103. In the second round of K-means clustering, the saturation is adopted as the standard for selecting reference points, and six reference points are determined according to a difference between a maximum value and a minimum value of the saturation of the pixels of the background-subtracted image 103. Accordingly, by performing one-dimensional K-means clustering on the pixels of the background-subtracted image 103 according to the six reference points, the pixels that are not classified as the background part in the first round of K-means clustering can be further determined and removed from the background-subtracted image 103 to update the background-subtracted image 103. It shall be appreciated that, the criterion for dividing the pixels into the cell part and the background part according to the clustering result may be determined by a user or by a preset threshold, thereby determining the pixels in which groups belong to the cell part and the pixels in the remaining groups belong to the background part.

After the above two rounds of one-dimensional K-means clustering, the processor 15 performs the third round of K-means clustering on the pixels of the background-subtracted image 103 to divide the pixels into a nuclear part 1201 and a cytoplasmic part 1203. Different from the first two rounds of K-means clustering, in the third round of K-means clustering, the processor 15 performs two-dimensional K-means clustering according to a weight proportion between the saturation and the value, e.g., performs the two-dimensional K-means clustering according to a weight proportion of 5:3 between the saturation and the value.

If the maximum value of the saturation of the pixels is 80 and the minimum value thereof is 30, then values of the first dimension of the two-dimensional initial reference points are respectively 30, 40, 50, 60, 70 and 80 with respect to the saturation. On the other hand, if the maximum value of the value of the pixels is 100 and the minimum value thereof is 25, then values of the second dimension of the two-dimensional initial reference points are respectively 25, 40, 55, 70, 85 and 100 with respect to the value. Therefore, six two-dimensional initial reference points are respectively (30, 25), (40, 40), (50, 55), (60, 70), (70, 85) and (80, 100). Thus, when the processor 15 performs the two-dimensional K-means clustering, the distance between each pixel and the reference point is equal to $$\sqrt{\frac{5}{8}(\Delta d1)^2 + \frac{3}{8}(\Delta d2)^2},$$

wherein $\Delta d1$ is the saturation difference, and $\Delta d2$ is the value difference.

As another example, when the color space is the RGB color space (i.e., formed by three attributes, namely, red, green and blue), the processor 15 may perform three rounds of K-means clustering with respect to at least one of the three attributes (i.e., red, green and blue). The first two rounds of clustering aim at removing the background part, while the third round of clustering aims at distinguishing the cytoplasmic part from the nuclear part. In detail, in the first round of K-means clustering, green is adopted as the standard, and a difference between a maximum value and a minimum value of the green of the pixels is divided into six equal parts to determine six initial reference points.

If the maximum value of the green of the pixels is 95 and the minimum value thereof is 10, then green of the six initial reference points are respectively 10, 27, 44, 61, 78 and 95. Accordingly, the pixels of the cytological image 101 may be divided into six groups by performing one-dimensional K-means clustering on the pixels according to the six initial reference points, and the pixels are divided into a cell part and a background part according to the six groups. In this way, the processor 15 can remove the pixels classified as the background part to generate the background-subtracted image 103. Next, the second round of K-means clustering is performed. Different from the first round of K-means clustering, the second round of K-means clustering adopts blue as the standard to execute same operations. Thus, the pixels that are not classified as the background part in the first round of K-means clustering can be further determined and removed from the background-subtracted image 103 to update the background-subtracted image 103. After the above two rounds of one-dimensional K-means clustering, the processor 15 performs the third round of K-means clustering on the pixels of the background-subtracted image 103 to divide the pixels into a nuclear part 1201 and a cytoplasmic part 1203. Similarly, the third round adopts red as the standard to execute the same operations as described above.

Figure 11:
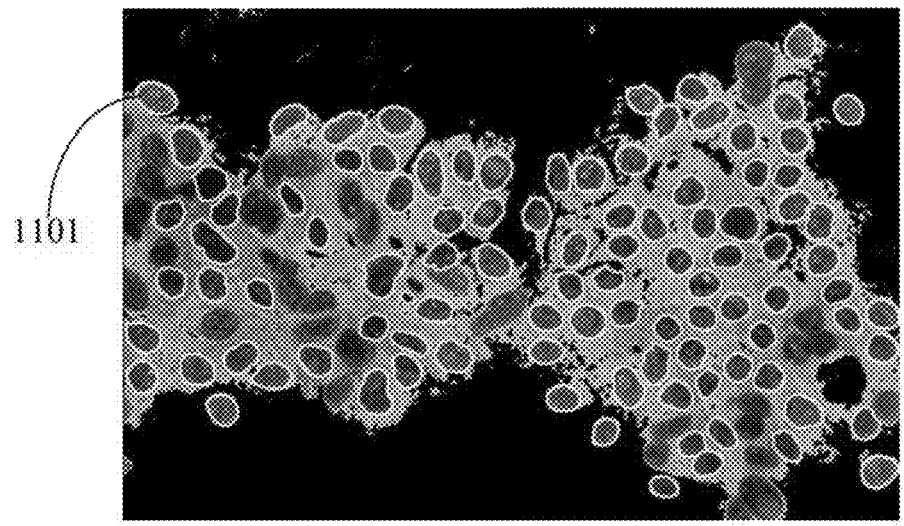
FIG. 11 depicts the visualization of segmented nuclear blocks.

After the pixels of the background-subtracted image 103 are divided into the nuclear part 1201 and the cytoplasmic part 1203, the processor 15 executes step S207 to detect a plurality of edge pixels in the background-subtracted image 103. In this way, after the edge pixels in the background-subtracted image 103 are detected, the processor 15 can connect those edge pixels to segment a plurality of nuclear blocks 1101 (which represents the nuclei) in the background-subtracted image 103, as shown in FIG. 11.

Thereafter, in step S209, the processor 15 generates a parameter set according to the nuclear blocks 1101, the nuclear part 1201, and the cytoplasmic part 1203. The parameter set may include at least one of the following: a nuclear polarity, an index of intranuclear cytoplasmic pseudoinclusions, a nuclei-to-cytoplasm color ratio and an index of nuclear overlapping and molding. The nuclei-to-cytoplasm color ratio is generated according to the nuclear part and the cytoplasmic part, the nuclear polarity is generated according to the nuclear blocks, the index of intranuclear cytoplasmic pseudoinclusions is generated according to the nuclear part, and the index of nuclear overlapping and molding is generated according to the nuclear blocks and the nuclear part.

Figure 9:
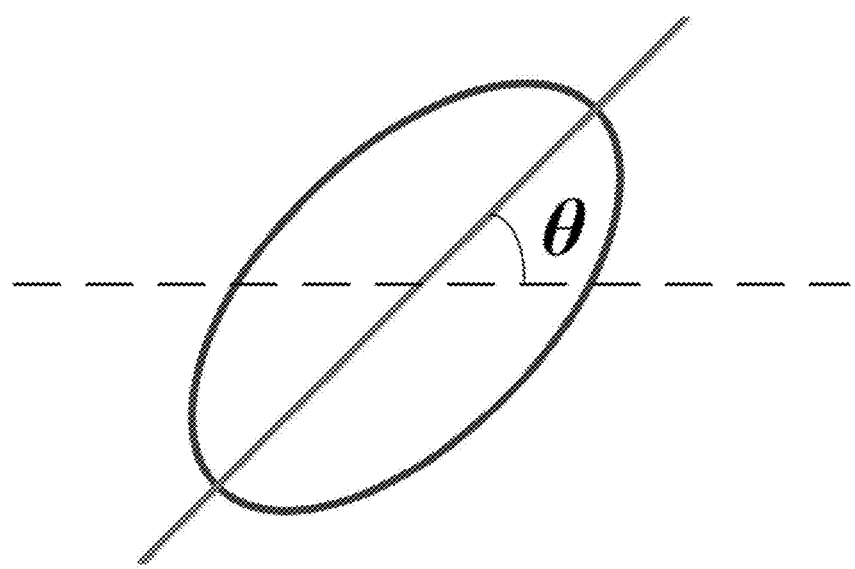
FIG. 9 depicts an angle between a nuclear major axis and a horizontal line.
Figure 15:
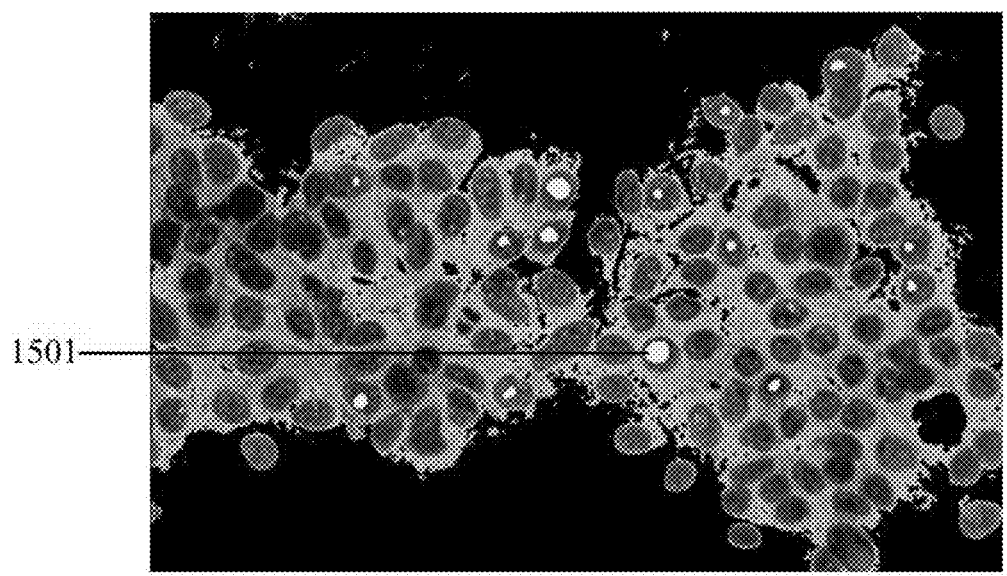
FIG. 15 depicts the visualization of intranuclear cytoplasmic pseudoinclusion blocks.

For example, the nuclear polarity may be generated by calculating a standard deviation of an angle between a nuclear major axis of the segmented nuclei and a horizontal line (the way in which the angle is calculated is as shown in FIG. 9). As another example, the index of intranuclear cytoplasmic pseudoinclusions may be generated by dividing a total area of a plurality of intranuclear cytoplasmic pseudoinclusions 1501 (as shown in FIG. 15) by a total area of the nuclear part 1201.

As another example, the nuclei-to-cytoplasm color ratio may be a hyperchromasia index which may be generated by dividing a function value of the color attributes of the nuclear part by a function value of the color attributes of the cytoplasmic part. For example, in the HSV color space, the hyperchromasia index may be a nucleus-to-cytoplasm saturation-value ratio or a nucleus-to-cytoplasm hue-value ratio. The nucleus-to-cytoplasm saturation-value ratio may be generated by dividing a ratio (i.e., a function value) of the average saturation to the average value of the nuclear part by a ratio (i.e., a function value) of the average saturation to the average value of the cytoplasmic part. The nucleus-to-cytoplasm hue-value ratio may be generated by dividing a ratio of the average hue to the average value of the nuclear part by a ratio of the average hue to the average value of the cytoplasmic part. Moreover, the hyperchromasia index may also be a nucleus-to-cytoplasm hue ratio or a nucleus-to-cytoplasm saturation ratio. The nucleus-to-cytoplasm hue ratio may be generated by dividing an average hue value (i.e., a function value) of the nuclear part by an average hue value (i.e., a function value) of the cytoplasmic part. The nucleus-to-cytoplasm saturation ratio may be generated by dividing an average saturation value (i.e., a function value) of the nuclear part by an average saturation value (i.e., a function value) of the cytoplasmic part.

Figure 10:
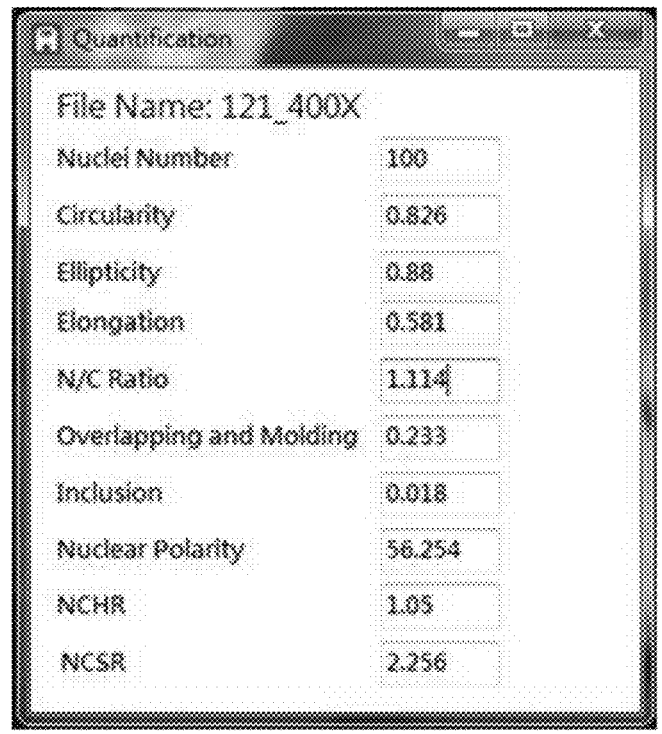
FIG. 10 depicts a quantified parameter set.

As another example, the index of nuclear overlapping and molding may be generated by dividing a remaining area not belonging to the nuclear blocks 1101 in the nuclear part by the total area of the nuclear part 1201. It shall be appreciated that, as shown in FIG. 10, these relevant quantified parameters may be determined by the user or by a preset standard. Relevant operations for quantifying according to cytological characteristic information shall be readily appreciated by those skilled in the art, and thus will not be further described herein.

As mentioned above, the nuclei-to-cytoplasm color ratio can be generated according to the nuclear part 1201 and the cytoplasmic part 1203, the nuclear polarity can be generated according to the nuclear blocks 1101, the index of intranuclear cytoplasmic pseudoinclusions can be generated according to the nuclear part 1201, and the index of nuclear overlapping and molding can be generated according to the nuclear blocks 1101 and the nuclear part 1201. In other words, after step S205 has been executed to divide the pixels in the background-subtracted image 103 into the nuclear part 1201 and the cytoplasmic part 1203, the processor 15 can immediately calculate the nuclei-to-cytoplasm color ratio according to the nuclear part 1201 and the cytoplasmic part 1203 without waiting until step S207 has been executed to segment the nuclear blocks 1101 in the background-subtracted image 103.

It shall be appreciated that, figures in the embodiments of the present invention are cytological images after being processed by Riu's stain. Taking the hyperchromasia index as an example, colors for staining the nucleus and the cytoplasm consist of blue and purple (purple is formed by red and blue), cell pathological changes will influence the coloration result of the Riu's stain, make the color denser or lighter, cause differences in the hue and the saturation of the nucleus and the cytoplasm. In addition, the increase in the value of both the nucleus and the cytoplasm will also cause differences in the red part and the blue part of the nucleus and the cytoplasm. Although different staining methods may cause different staining effects, relevant operations for adjusting the weight/attribute proportion depending on different staining methods shall be appreciated by those of ordinary skill in the art, and thus will not be further described.

As another example, the index of intranuclear cytoplasmic pseudoinclusions may be calculated using Equation 1, and the area determined as the intranuclear cytoplasmic pseudoinclusion blocks 1501 is divided by the total area of the nuclear part 1201 to obtain a proportion of the intranuclear cytoplasmic pseudoinclusion blocks 1501.

$$\text{Index of intranuclear cytoplasmic pseudoinclusions} = \frac{area_{inclusions}}{area_{nuclei}}, \quad \text{(Equation 1)}$$

wherein $area_{inclusions}$ is the total area of the intranuclear cytoplasmic pseudoinclusion blocks 1501, and $area_{nuclei}$ is the total area of the nuclear part 1201.

Additionally, the index of nuclear overlapping and molding is calculated using Equation 2 by dividing a remaining area not belonging to the nuclear blocks 1101 in the nuclear part by an area of the nuclear part. In other words, the index of nuclear overlapping and molding represents the proportion occupied by the overlapped and molded nuclear area (including areas of nuclei of which the edge is broken and irregular and overlapped nuclei) in the nuclear part.

$$\text{Index of nuclear overlapping and molding} = \quad \text{(Equation 2)}$$
$$1 - \frac{area_{discrete\ nuclei}}{area_{nuclei}},$$

wherein area$_{discrete\ nuclei}$ is the total area of the nuclear blocks 1101, and area$_{nuclei}$ is the total area of the nuclear part 1201.

In some embodiments, the parameter sets further comprise parameters such as an area, a circularity, an ellipticity, and an elongation or the like. For example, the elongation of a nucleus may be calculated using Equation 3.

$$\text{Elongation} = \sqrt{1 - \frac{\left(\frac{d_2}{2}\right)^2}{\left(\frac{d_1}{2}\right)^2}}, \qquad \text{(Equation 3)}$$

wherein $d_1$ is a major-axis length of the nuclear block, and $d_2$ is a minor-axis length of the nuclear block.

Figure 13:
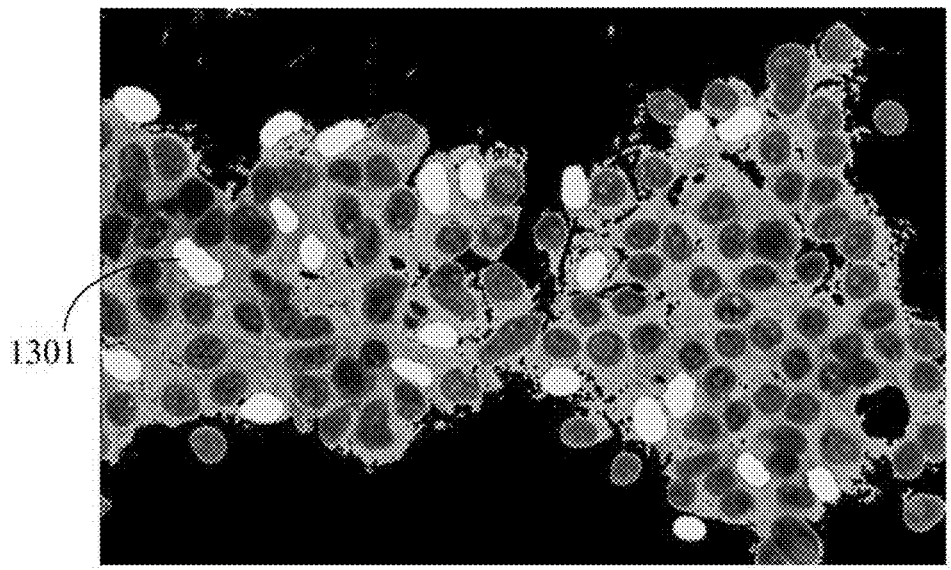
FIG. 13 depicts the visualization of at least one elongated nuclear block among the nuclei.
Figure 14:
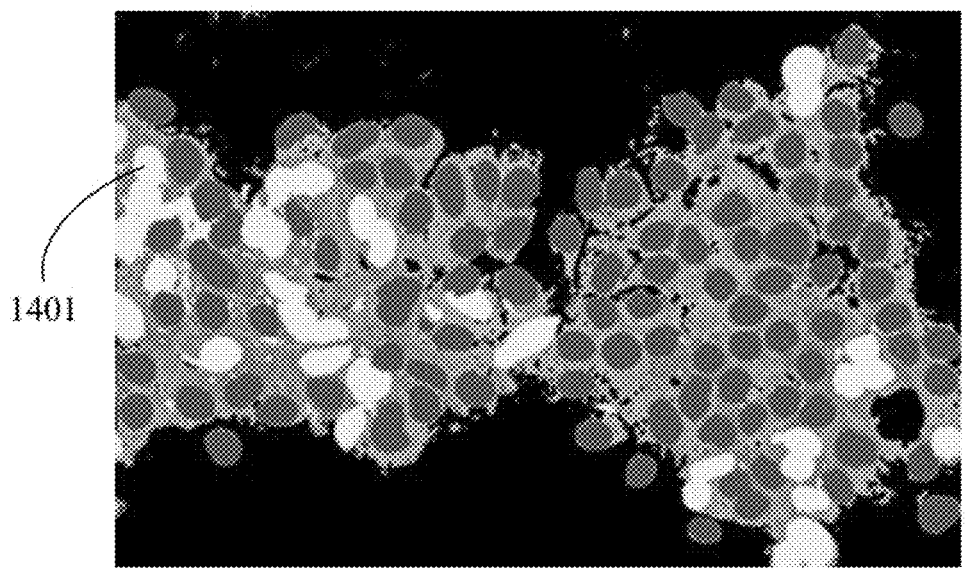
FIG. 14 depicts the visualization of an overlapped and molded nuclei in the nuclear part.
Figure 16:
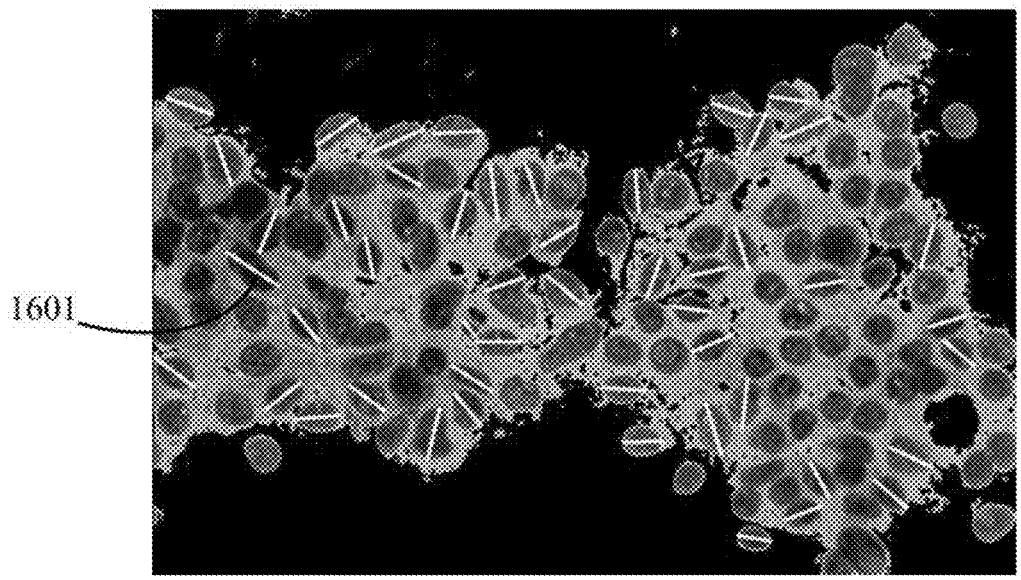
FIG. 16 depicts the visualization of a nuclear major-axis distribution.

Finally, the processor 15 executes step S211 to visualize the background-subtracted image 103 to generate an output image 105 to present the nuclear blocks 1101, the nuclear part 1201, and the cytoplasmic part 1203. For example, in FIG. 12, the output image 105 is used to visualize a nuclei-to-cytoplasm ratio (NCR) of the nuclear part 1201 and the cytoplasmic part 1203; in FIG. 11, the output image 105 is used to visualize the segmented nuclei 1101; in FIG. 13, the output image 105 is used to visualize an elongated nuclear block 1301 among the nuclei; in FIG. 14, the output image 105 is used to visualize an overlapped nuclear part 1401 in the nuclear part; in FIG. 15, the output image 105 is used to visualize intranuclear cytoplasmic pseudoinclusion blocks 1501; and in FIG. 16, the output image 105 is used to visualize a nuclear major-axis distribution (e.g., a nuclear major axis 1601).

As can be known from above descriptions, the method for quantifying characteristics of cytological image according to the present invention may be divided into three stages of operation: the first stage is the clustering stage, the second stage is the edge detection stage, and the third stage is a stage for calculating relevant parameters of nuclear morphology and visualizing characteristics. The operation in the clustering stage has been described with exemplary examples in this embodiment, and the edge detection stage and the stage for calculating relevant parameters of nuclear morphology and visualizing characteristics will be detailed hereinafter in subsequent embodiments.

Figure 2B:
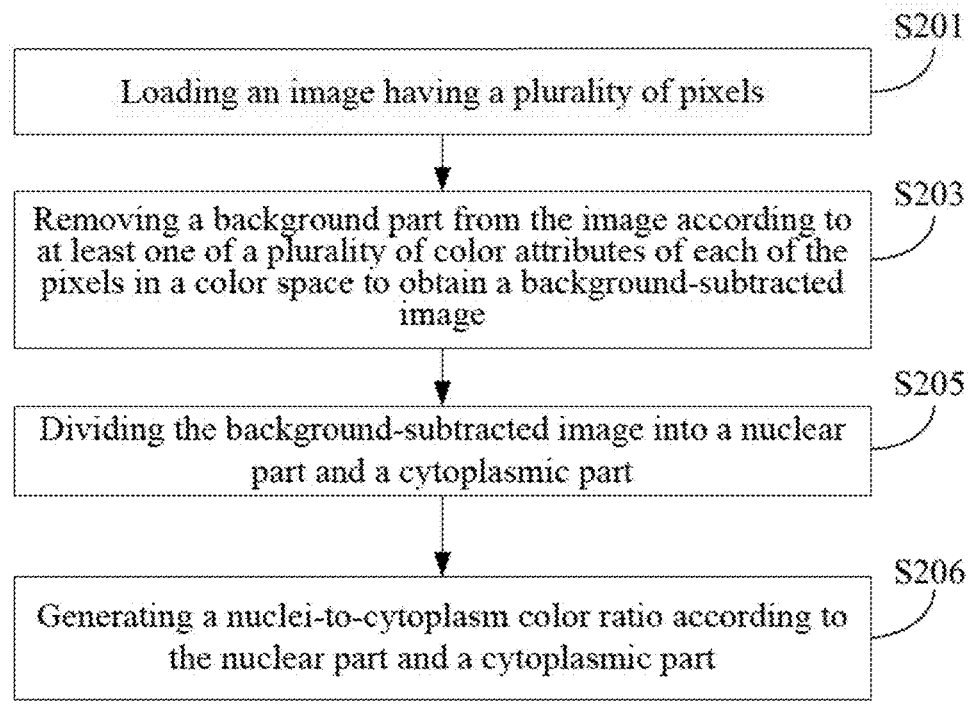
FIGS. 2B and 2C are flowchart diagrams respectively depicting methods for quantifying characteristics of cytological image according to the other embodiments of the present invention.

It shall be appreciated that, after generating the nuclei-to-cytoplasm color ratio, the processor 15 can provide the information of the generated nuclei-to-cytoplasm color ratio to the user via a display or an output device etc. Therefore, in other embodiments, the user can set up the image processing device 1 to only generate the nuclei-to-cytoplasm color ratio and does not need to execute the subsequent steps of segmenting the nuclear blocks, generating other parameters based on the nuclear blocks, visualizing the background-subtracted image etc. As shown in FIG. 2B, after executing step S205 to divide the pixels in the background-subtracted image 103 into the nuclear part 1201 and the cytoplasmic part 1203, the processor 15 may only execute step S206 to generate the nuclei-to-cytoplasm color ratio according to the nuclear part 1201 and the cytoplasmic part 1203. In other words, the users can choose the parameters needing to be outputted based their demand and make the processor 15 to only execute the steps corresponding to the chosen parameters without executing all steps.

Figure 2C:
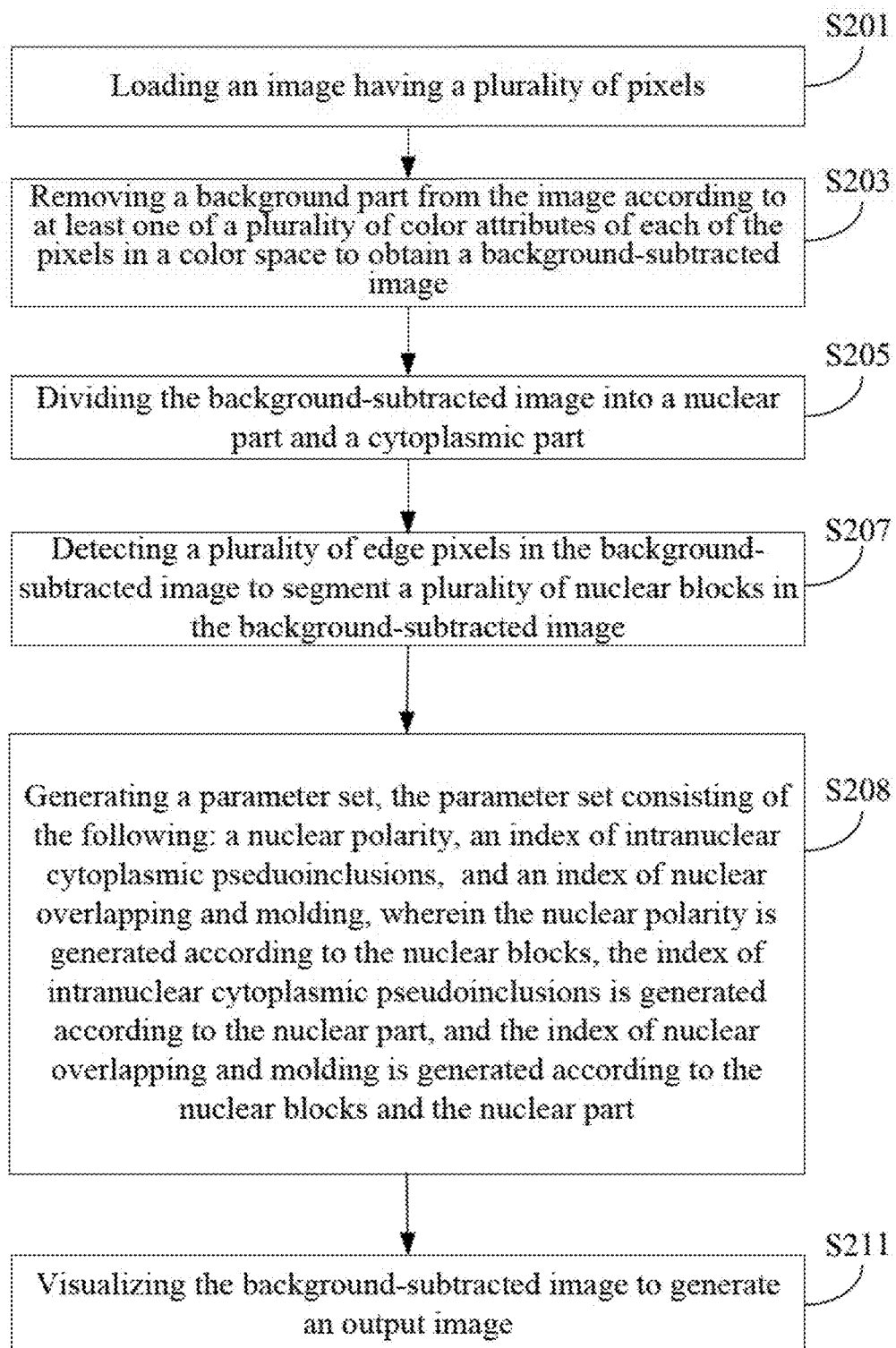

In addition, in other embodiments, based on the parameters chosen by the user, step 209 in FIG. 2A can be replaced by step 208, as shown in FIG. 2C. In this case, the generated parameter set may include the nuclear polarity, the index of intranuclear cytoplasmic pseudoinclusions, and the index of nuclear overlapping and molding, and does not include the nuclei-to-cytoplasm color ratio.

Figure 3:
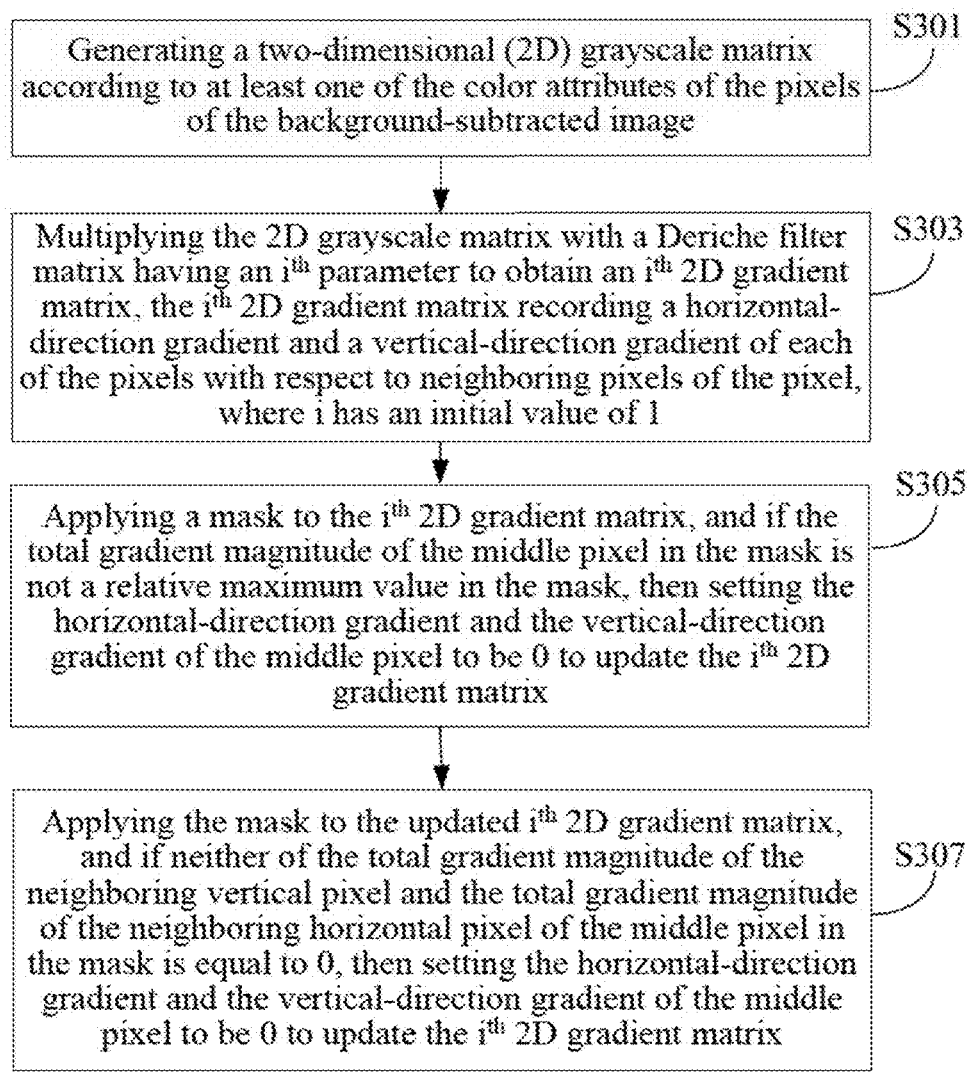
Figure 4B:
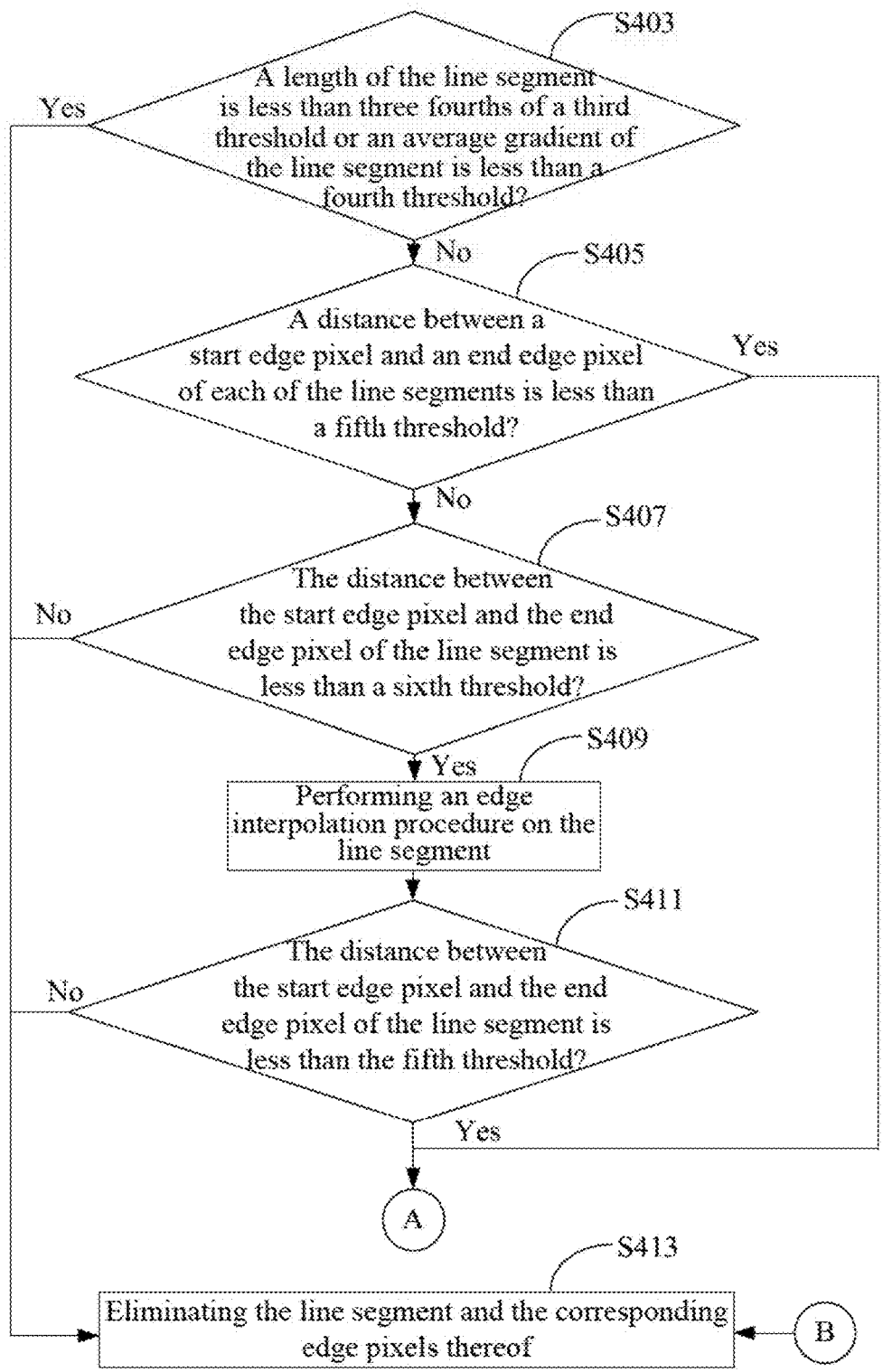
Figure 4C:
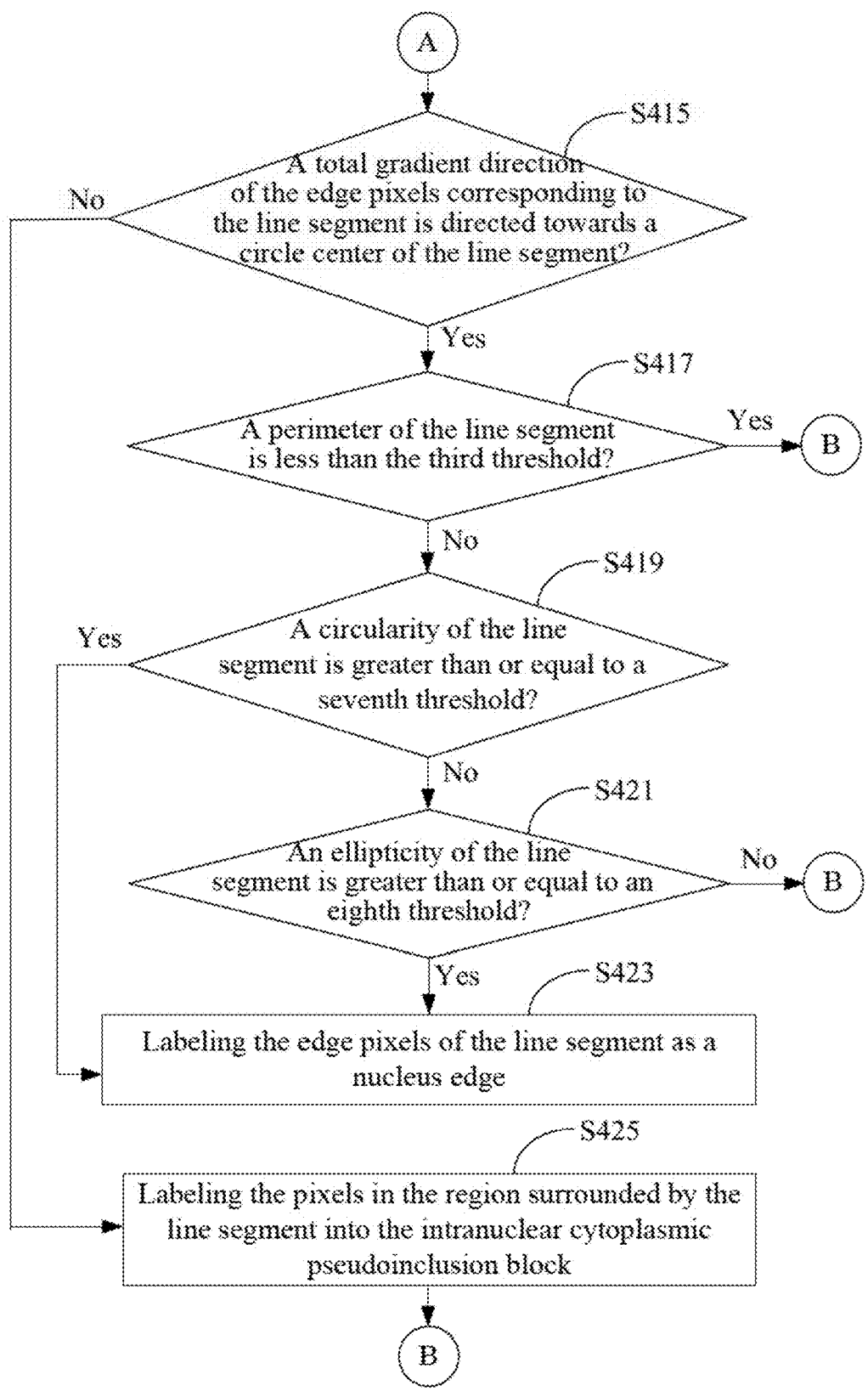
Figure 5:
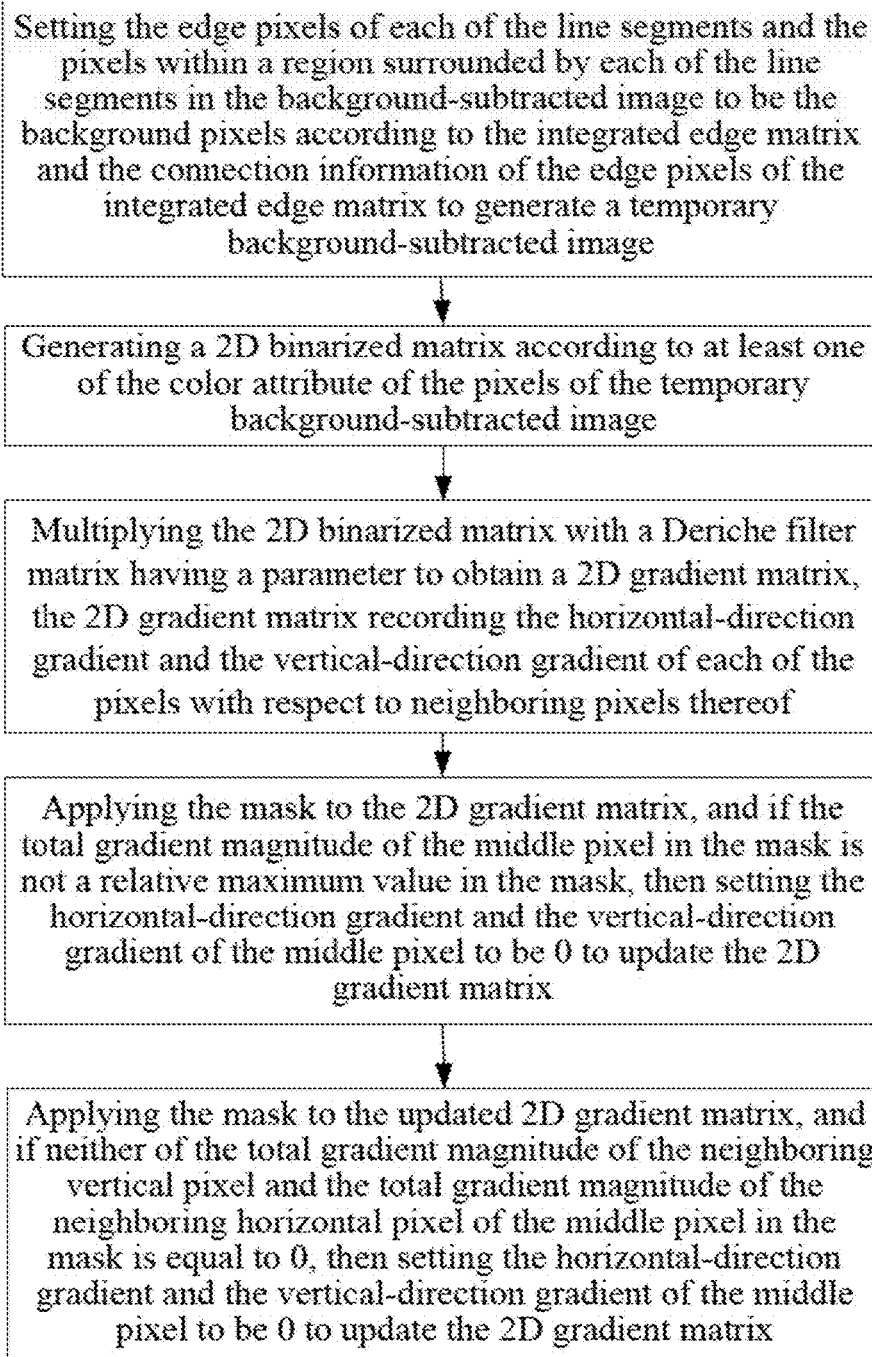

Please refer to FIG. 3 to FIG. 4C together for a second embodiment of the present invention. The second embodiment is an extension of the first embodiment, and it describes operations relevant to the edge detection stage. That is, the step S207 of the first embodiment further comprises steps shown in FIG. 3, FIG. 4A, FIG. 4B and FIG. 4C. First, in step S301, the processor 15 generates a two-dimensional (2D) grayscale matrix according to at least one of the color attributes of the pixels of the background-subtracted image 103.

Figure 8A:
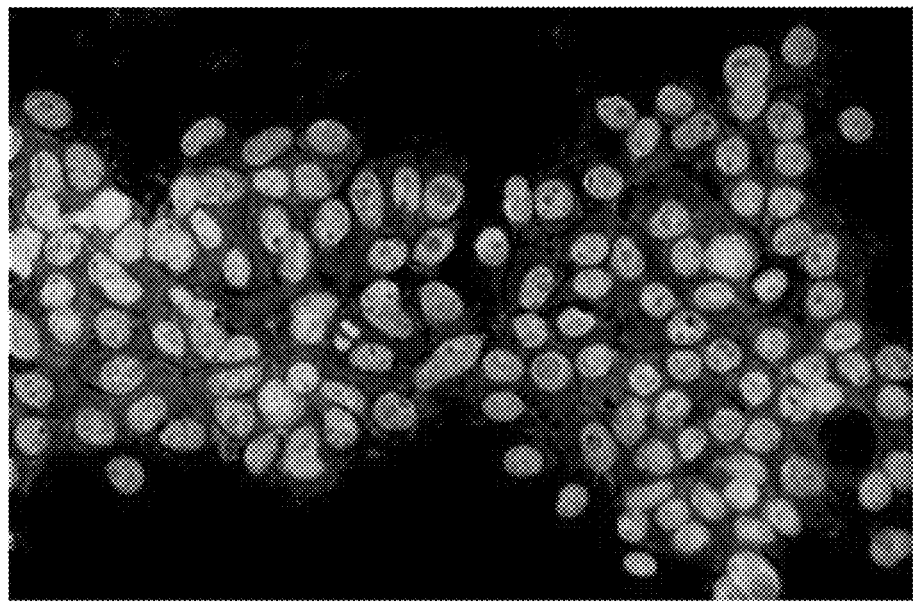
FIG. 8A depicts a grayscale image.

For example, in the HSV color space, the processor 15 converts the background-subtracted image 103 into a grayscale image 105 according to a weight proportion of 5:−3 between the saturation and the value, as shown in FIG. 8A. Each pixel of the grayscale image 105 has a grayscale value, so the processor may represent the grayscale values of the pixels in a 2D grayscale matrix. It shall be appreciated that, the above weight proportion is for purpose of illustration rather than to limit the present invention. Furthermore, in the RGB color space, how to convert the background-subtracted image 103 into the grayscale image 105 shall also be appreciated by those of ordinary skill in the art and thus will not be further described herein.

Next, in step S303, the processor 15 multiplies the 2D grayscale matrix with a Deriche filter matrix having an $i^{th}$ parameter to obtain an $i^{th}$ 2D gradient matrix, where i is 1 to 3. The $i^{th}$ 2D gradient matrix records a horizontal-direction gradient ($D_x$) and a vertical-direction gradient ($D_y$) of each of the pixels with respect to neighboring pixels of the pixel. The $i^{th}$ parameter is a Gaussian distribution parameter, so the Deriche filter matrices having different parameters are used to blur the grayscale image 105 at different levels to reduce noise in the grayscale image 105.

Thereafter, in step S305, the processor 15 applies a mask to the $i^{th}$ 2D gradient matrix. For example, the mask is a 3×3 matrix, and the processor 15 uses the mask to inspect the horizontal-direction gradient and the vertical-direction gradient of the pixels in each 3×3 submatrix of the $i^{th}$ 2D gradient matrix so as to find pixels which may be edge pixels. In detail, the processor 15 determines whether a total gradient magnitude of a middle pixel in the current mask is a relative maximum value in the mask, and if the total gradient magnitude of the middle pixel in the mask is not the relative maximum value in the mask, then the processor 15 sets the horizontal-direction gradient and the vertical-direction gradient of the middle pixel in the current mask to be 0 (i.e., non-maximal suppression).

For example, the processor 15 determines the intensity of the middle pixel in the mask and two pixels respectively located before and after the middle pixel in the gradient direction of the middle pixel. If the total gradient magnitude of the middle pixel is greater than those of the above two pixels, then the total gradient magnitude of the middle pixel is retained; and otherwise, the total gradient magnitude is set to be 0, thereby updating the $i^{th}$ 2D gradient matrix. It shall be appreciated that, when the gradient direction is not located at pixels in the mask (e.g., not be 0 degree, 45 degrees, 90 degrees, 135 degrees, 180 degrees, . . . , 360 degrees), a virtual pixel may be obtained as the gradient direction by performing interpolation on pixels around the path.

As another example, in another non-maximal suppression method, the processor 15 may determine whether a total gradient magnitude of a middle pixel in the current mask is smaller than a plurality of total gradient magnitudes of all of the neighboring pixels. If the determination result is yes, then it means that the middle pixel should not be the edge pixel. Thus, the processor 15 sets the horizontal-direction gradient and the vertical-direction gradient of the middle pixel in the current mask to be 0 to update the $i^{th}$ 2D gradient matrix. The total gradient magnitude of each of the pixels is calculated based on Equation 4.

$$\text{Total gradient magnitude} = \sqrt{D_x^2 + D_y^2} \quad \text{(Equation 4)}$$

Figure 8B:
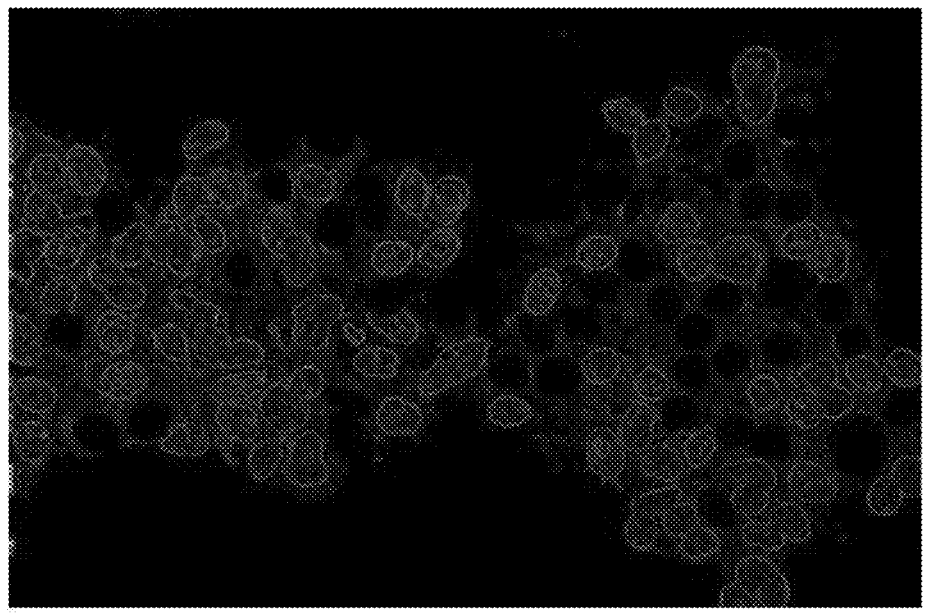
FIG. 8B depicts edge pixels of the background-subtracted image.

After the step S305 is executed, the pixels having the horizontal-direction gradient and the vertical-direction gradient not equal to 0 in the updated $i^{th}$ 2D gradient matrix are preliminarily determined as the edge pixels. Next, the processor 15 performs a thinning method on the pixels that are preliminarily determined as the edge pixels, i.e., executes step S307 aiming at further sharpening these edge pixels. In the step S307, the processor 15 reapplies the mask to the updated $i^{th}$ 2D gradient matrix to determine in sequence whether neither of the total gradient magnitude of a neighboring vertical pixel and the total gradient magnitude of a neighboring horizontal pixel of the middle pixel in the current mask is equal to 0. If neither of the total gradient magnitude of the neighboring vertical pixel and the total gradient magnitude of the neighboring horizontal pixel of the middle pixel in the current mask is equal to 0, then the processor 15 sets the horizontal-direction gradient and the vertical-direction gradient of the middle pixel in the current mask to be 0 to update the $i^{th}$ 2D gradient matrix again. In this way, the pixels having the total gradient magnitude not equal to 0 in the updated $i^{th}$ 2D gradient matrix are determined as the edge pixels, as shown in FIG. 8B.

The processor 15 executes the steps as shown in FIG. 4A to FIG. 4C to connect the pixels that are determined as the edge pixels in above $i^{th}$ 2D gradient matrix, thereby segmenting a plurality of nuclear blocks 1101. First, in step S401, the processor 15 connects the edge pixels according to a 8-connection connectivity rule to form a plurality of line segments. For each of the edge pixels which have not been connected, the processor 15 determines whether the total gradient magnitude of a next edge pixel to be connected to a current edge pixel is greater than a first threshold and determines whether an angle between a total gradient direction of the current edge pixel and a total gradient direction of the next edge pixel to be connected to the current edge pixel is less than a second threshold. For example, the total gradient direction may be calculated based on Equation 5.

$$\text{Total gradient direction} = \tan^{-1}\frac{D_y}{D_x} \quad \text{(Equation 5)}$$

When the total gradient magnitude of the next edge pixel to be connected is greater than the first threshold and the angle is less than the second threshold, the processor 15 connects the current edge pixel to the next edge pixel, and takes the next edge pixel that has been connected as the current edge pixel. Thereafter, the processor 15 continues to determine whether a next edge pixel is available for connection, and connects the next edge pixel if the determination result is yes. Thus, a line segment is formed until it is determined that no next edge pixel is available for connection. Then, the processor 15 makes the determinations as shown in following steps on each of the above-mentioned line segments to determine the edge pixels on which line segments are the edge pixels of a normal nucleus.

In step S403, the processor 15 determines whether a length of the line segment is less than three fourths of a third threshold or whether an average gradient of the pixels of the line segment is less than a fourth threshold, thereby eliminating the line segment, a length of which is excessively short or an average gradient of which is excessively small. When the length of the line segment is less than three fourths of the third threshold or the average gradient of the pixels of the line segment is less than the fourth threshold, the processor 15 executes step S413 to eliminate the line segment and corresponding edge pixels thereof. It shall be appreciated that, the above third threshold may be an edge perimeter of a normal nucleus.

Thereafter, in order to determine whether the line segments are generally closed curves, the processor 15 further executes step S405 to determine whether a distance between a start edge pixel (i.e., the start point) and an end edge pixel (i.e., the end point) of each of the line segments is less than a fifth threshold. If the distance between the start edge pixel and the end edge pixel of the line segment is less than the fifth threshold, then it means that the line segment is generally a closed curve and the region surrounded by the line segment may be the nuclear block. Next, the processor 15 executes step S415 if the distance between the start edge pixel and the end edge pixel of the line segment is less than the fifth threshold.

Moreover, if the distance between the start edge pixel and the end edge pixel of the line segment is not less than the fifth threshold, then the processor 15 executes step S407 to determine whether the distance between the start edge pixel and the end edge pixel of the line segment is less than a sixth threshold. If the distance between the start edge pixel and the end edge pixel of the line segment is less than the sixth threshold, then it means that it is possible to make the distance between the start edge pixel and the end edge pixel of the line segment become less than the fifth threshold by performing an edge interpolation procedure. Thus, the processor 15 executes step S409 to perform the edge interpolation procedure on the line segment. It shall be appreciated that, the sixth threshold may be a value obtained by multiplying the length of the line segment with a certain ratio, e.g., 0.25. That is, the line segment may allow a distance (i.e., an unconnected line segment) between the start edge pixel and the end edge pixel thereof that is not more than at most a quarter of the length of the line segment.

For example, in the edge interpolation procedure, the processor 15 may calculate a vertical distance and a horizontal distance between the start edge pixel and the end edge pixel, and determine whether the horizontal distance is greater than the vertical distance. If the horizontal distance is greater than the vertical distance, then the edge interpolation procedure is started from the horizontal direction. Each time the horizontal direction moves forward by one pixel, the vertical direction moves forward along the slope of the line connecting the start edge pixel with the end edge pixel. On the contrary, if the horizontal distance is not greater than the vertical distance, then the edge interpolation procedure is started from the vertical direction. Each time the vertical direction moves forward by one pixel, the horizontal direction moves forward along the slope of the line connecting the start edge pixel with the end edge pixel.

After the edge interpolation procedure is performed, the processor 15 executes step S411 to determine whether the distance between the start edge pixel and the end edge pixel of the line segment on which the edge interpolation procedure is performed has become less than the fifth threshold. If the distance between the start edge pixel and the end edge pixel of the line segment is still not less than the fifth threshold, then it means that the unconnected line segment cannot be made up by the edge interpolation procedure. Therefore, the processor 15 executes step S413 to eliminate the line segment and the corresponding edge pixels thereof. On the contrary, if the distance between the start edge pixel and the end edge pixel of the line segment has become less than the fifth threshold, then the processor 15 executes step S415.

Next, in step S415, the processor 15 determines whether a total gradient direction of the edge pixels corresponding to the line segment is directed towards a circle center of the line segment (i.e., a circle center of a region surrounded by the line segment) to determine whether the pixels in the region surrounded by the line segment belong to an intranuclear cytoplasmic pseudoinclusion block. Generally speaking, the value of the cytoplasm is greater than that of the nucleus, so the total gradient direction of the edge pixels of the cytoplasm is directed towards the edge pixels of the nucleus from the circle center, which is opposite to the case for the nucleus that the total gradient direction of the edge pixels of the nucleus is directed towards the circle center. Therefore, when the total gradient direction of the edge pixels corresponding to the line segment is not directed towards the circle center of the line segment, the processor 15 executes step S425 to label the pixels in the region surrounded by the line segment into the intranuclear cytoplasmic pseudoinclusion block, and executes step S413 to eliminate the line segment and the corresponding edge pixels thereof. It shall be appreciated that, the intranuclear cytoplasmic pseudoinclusion refers to that one or more spherical cytoplasm surrounded by a membrane and having cytoplasm organelles are included in the nucleus, and this is usually determined as a characteristic of malignancy. By this method, this kind of nuclei can be labeled to facilitate subsequent further determination. Thus, the pixels labeled into the intranuclear cytoplasmic pseudoinclusion block may be visualized subsequently as shown in FIG. 15.

When the total gradient direction of the edge pixels of the line segment is directed towards the circle center of the line segment, the processor 15 executes step S417 to determine whether a perimeter of the line segment is less than the third threshold. If the perimeter is less than the third threshold, then the processor 15 executes step S413 to eliminate the line segment and the corresponding edge pixels thereof. If the perimeter is not less than the third threshold, then the processor 15 executes step S419 to further determine whether a circularity of the line segment is greater than or equal to a seventh threshold. In detail, the processor 15 calculates the circularity of the line segment using the following Equation 6.

$$\text{Circularity} = \frac{4\pi \times A}{P^2}, \quad \text{(Equation 6)}$$

where A is an area surrounded by the line segment, and P is the perimeter of the line segment.

If the circularity of the line segment is greater than or equal to the seventh threshold, then the processor 15 executes step S423 to label the edge pixels of the line segment as a nucleus edge, and determine the line segment as a complete and nearly round nuclear edge. On the other hand, if the circularity of the line segment is less than the seventh threshold, then the processor 15 executes step S421 to determine whether an ellipticity of the line segment is greater than or equal to an eighth threshold. In detail, the processor 15 calculates the ellipticity of the line segment using the following Equation 7.

$$\text{Ellipticity} = \frac{A \times \left[3 \times (d_1 + d_2) - 2\sqrt{d_1 \times d_2}\right]}{d_1 \times d_2 \times P}, \quad \text{(Equation 7)}$$

where A is an area surrounded by the line segment, P is the perimeter of the line segment, $d_1$ is a major-axis length of the region surrounded by the line segment, and $d_2$ is a minor-axis length of the region surrounded by the line segment.

If the ellipticity of the line segment is greater than or equal to the eighth threshold, then the step S423 is executed to label the edge pixels of the line segment as a nucleus edge, and determine the line segment as a complete and elongated (elliptical) nuclear edge. Subsequently, the elongated nuclear edges are visualized to present at least one elongated nuclear block among the nuclear blocks. On the contrary, if the ellipticity of the line segment is less than the eighth threshold, then the edge pixels of the line segment are determined as irregularly-shaped nuclear edge, and the step S413 is executed to eliminate the line segment and the corresponding edge pixels thereof.

Accordingly, the edge pixels of the line segments, which are not eliminated after the operations shown in FIG. 4B and FIG. 4C, are edge pixels of a normal nucleus. Thus, the processor 15 may generate an $i^{th}$ edge matrix and $i^{th}$ connection information of the edge pixels of the $i^{th}$ edge matrix for each $i^{th}$ 2D gradient matrix. Thereafter, the processor 15 integrates the $1^{st}$ edge matrix, the $2^{nd}$ edge matrix and the $3^{rd}$ edge matrix as well as the $1^{st}$ connection information, the $2^{nd}$ connection information and the $3^{rd}$ connection information to obtain an integrated edge matrix and integrated connection information of the edge pixels of the integrated edge matrix. In this way, in the edge detection stage, the processor 15 can segment the nuclear block in the background-subtracted image to a largest extent so as to prevent missing any nuclear block according to the integrated edge matrix and the integrated connection information of the edge pixels of the integrated edge matrix, and obtain intranuclear cytoplasmic pseudoinclusion blocks.

Additionally, the way in which the $1^{st}$ edge matrix, the $2^{nd}$ edge matrix and the $3^{rd}$ edge matrix as well as the $1^{st}$ connection information, the $2^{nd}$ connection information and the $3^{rd}$ connection information are integrated as mentioned above may be achieved by comparing barycenters of the line segments (i.e., the nuclear edges) in the $1^{st}$ edge matrix, the $2^{nd}$ edge matrix and the $3^{rd}$ edge matrix. For example, after the $2^{nd}$ edge matrix is obtained, the processor 15 determines whether there is at least one new line segment (i.e., the nuclear edge), a plurality of barycenter distances between a barycenter of which and a plurality of barycenters of the regions surround by the line segments (i.e., the nuclear regions) of the $1^{st}$ edge matrix are all greater than a nuclear average minor-axis length, among the line segments of the $2^{nd}$ edge matrix. If the barycenter distances are all greater than a nuclear average minor-axis length, then it means that the at least one new line segment does not exist in the $1^{st}$ edge matrix. Thus, the edge pixels of the at least one new line segment (i.e., the nuclear edge) are added into the $1^{st}$ edge matrix to generate the integrated edge matrix, and connection information associated with the at least one new line segment is added into the 1st connection information to generate the integrated connection information.

Similarly, after the integrated edge matrix and the integrated connection information are obtained, the processor 15 also determines whether there is at least one new line segment, a plurality of barycenter distances between a barycenter of which and a plurality of barycenters of the regions surrounded by the line segments (i.e., the nuclear regions) of the integrated edge matrix are all greater than a nuclear average minor-axis length, among the line segments of the $3^{rd}$ edge matrix. If the barycenter distances are all greater than a nuclear average minor-axis length, then it means that the at least one new line segment does not exist in the integrated edge matrix. Thus, the edge pixels of the at least one new line segment (i.e., the nuclear edge) are added into the integrated edge matrix to update the integrated edge matrix, and connection information associated with the at least one new line segment is added into the integrated connection information to update the integrated connection information. In this way, the processor 15 can integrate the $1^{st}$ edge matrix, the $2^{nd}$ edge matrix and the $3^{rd}$ edge matrix as well as the $1^{st}$ connection information, the $2^{nd}$ connection information and the $3^{rd}$ connection information by comparing the barycenters of the regions surround by the line segments (i.e., nuclear regions).

It shall be appreciated that, three edge matrices and the corresponding connection information thereof are generated in the above embodiment as an exemplary example. However, as shall be appreciated by those of ordinary skill in the art based on the above description, the present invention may also only integrate two edge matrices and the corresponding connection information thereof, or the present invention may also generate and integrate more than three edge matrices and the corresponding connection information thereof. Accordingly, the generation and the integration of any number of edge matrices and the corresponding connection information thereof shall all fall within the scope of the present invention.

A third embodiment of the present invention is a further extension of the second embodiment. In this embodiment, after several edge matrices and the corresponding connection information thereof are obtained and before these edge matrices and the corresponding connection information thereof are integrated, the processor 15 may reconfirm whether any other line segment may be the nuclear edge in each of the edge matrices based on the edge pixels of the line segments and the background-subtracted image 103.

Specifically, the processor 15 sets the pixels within a region surrounded by each of the line segments (i.e., the complete nuclear edges) in the background-subtracted image 103 as background pixels according to the $i^{th}$ edge matrix and the $i^{th}$ connection information thereof to generate a temporary background-subtracted image 103_temp. It shall be appreciated that, the present invention may perform appropriate normalization processing on the temporary background-subtracted image first to further highlight the pixels of the temporary background-subtracted image.

Thereafter, similar to the step S301, the processor 105 converts the temporary background-subtracted image 103_temp into a grayscale image to generate a 2D grayscale matrix, and executes the steps S303 to S307 and the steps S401 to S425 for the 2D grayscale matrix to obtain the $i^{th}$ edge matrix and the $i^{th}$ connection information of the temporary background-subtracted image 103_temp.

Thereafter, the processor 15 determines whether there are edge pixels in the $i^{th}$ edge matrix and the $i^{th}$ connection information of the temporary background-subtracted image 103_temp. If there are the edge pixels, then it means that the region surrounded by the line segment connecting the edge pixels is the nuclear block. Therefore, the $i^{th}$ edge matrix and the $i^{th}$ connection information of the temporary background-subtracted image 103_temp are incorporated into the $i^{th}$ edge matrix and the $i^{th}$ connection information of the background-subtracted image 103 respectively.

Thereafter, the processor 15 generates a new temporary background-subtracted image 103_temp based on the $i^{th}$ edge matrix and the $i^{th}$ connection information of the updated background-subtracted image 103. Similarly, the processor 105 converts the new temporary background-subtracted image 103_temp into a grayscale image to generate a 2D grayscale matrix, and executes the steps S303 to S307 and the steps S401 to S425 for the 2D grayscale matrix to incorporate the $i^{th}$ edge matrix and the $i^{th}$ connection information of the new temporary background-subtracted image 103_temp into the $i^{th}$ edge matrix and the $i^{th}$ connection information of the background-subtracted image 103 respectively. In this way, through the above operations, the processor 15 can continuously generate new temporary background-subtracted images 103_temp and incorporate the $i^{th}$ edge matrix and the $i^{th}$ connection information of the new temporary background-subtracted images 103_temp into the $i^{th}$ edge matrix and the $i^{th}$ connection information of the background-subtracted image 103 respectively, until there is no edge pixel (i.e., the nuclear edge) in the new temporary background-subtracted images 103_temp, which means that there is no more nuclear block which can be segmented in the temporary background-subtracted images 103_temp.

A fourth embodiment of the present invention is also a further extension of the second embodiment. In this embodiment, after the edge matrices and the corresponding connection information thereof are integrated, the processor 15 may reconfirm whether any other line segment may be the nuclear edge based on the edge pixels of the line segments and the background-subtracted image 103.

In detail, the processor 15 executes step S501 to set the edge pixels of each of the line segments and the pixels within a region surrounded by each of the line segments (i.e., the complete nuclear edges) in the background-subtracted image 103 to be the background pixels according to the integrated edge matrix and the connection information of the edge pixels of the integrated edge matrix to generate a temporary background-subtracted image 103_temp. Next, the processor 15 converts the temporary background-subtracted images 103_temp into a black-and-white image to generate a 2D binarized matrix according to at least one of the color attributes of the pixels of the temporary background-subtracted image 103_temp. For example, in the HSV color space, the processor 15 converts the temporary background-subtracted images 103_temp into a black-and-white image to generate a 2D binarized matrix according to the value of the pixels of the temporary background-subtracted images 103_temp. For example, the processor 15 may adjust the pixels belonging to the nuclear part in the temporary background-subtracted images 103_temp to be the brightest and adjust the pixels belonging to the cytoplasmic part in the temporary background-subtracted images 103_temp to be the darkest to generate the black-and-white image. Moreover, how to convert the temporary background-subtracted images 103_temp into a black-and-white image in the RGB color space shall also be appreciated by those of ordinary skill in the art, and thus will not be further described herein.

Thereafter, the processor 15 executes step S505 to multiply the 2D binarized matrix with a Deriche filter matrix having a parameter to obtain a 2D gradient matrix. As described above, the 2D gradient matrix records the horizontal-direction gradient and the vertical-direction gradient of each of the pixels with respect to neighboring pixels thereof. Next, similar to step S305, the processor 15 executes step S507 to apply the mask to the 2D gradient matrix. When the total gradient magnitude of the middle pixel in the mask is not a relative maximum value in the mask, the horizontal-direction gradient and the vertical-direction gradient of the middle pixel are set to be 0 to update the 2D gradient matrix.

Thereafter, similar to step S307, the processor 15 executes step S509 to apply the mask to the updated 2D gradient matrix. When neither of the total gradient magnitude of the neighboring vertical pixel and the total gradient magnitude of the neighboring horizontal pixel of the middle pixel in the mask is equal to 0, the horizontal-direction gradient and the vertical-direction gradient of the middle pixel are set to be 0 to update the 2D gradient matrix. The pixels having the horizontal-direction gradient and the vertical-direction gradient not equal to 0 in the updated 2D gradient matrix are the edge pixels.

Next, similar to step S401, the processor 15 executes step S601 to connect the edge pixels according to the 8-connection connectivity rule to form a plurality of line segments. Different from what described previously, an angle between the total gradient direction of the current edge pixel and the total gradient direction of the next edge pixel connected to the current edge pixel needs to be less than a second threshold.

Figure 6B:
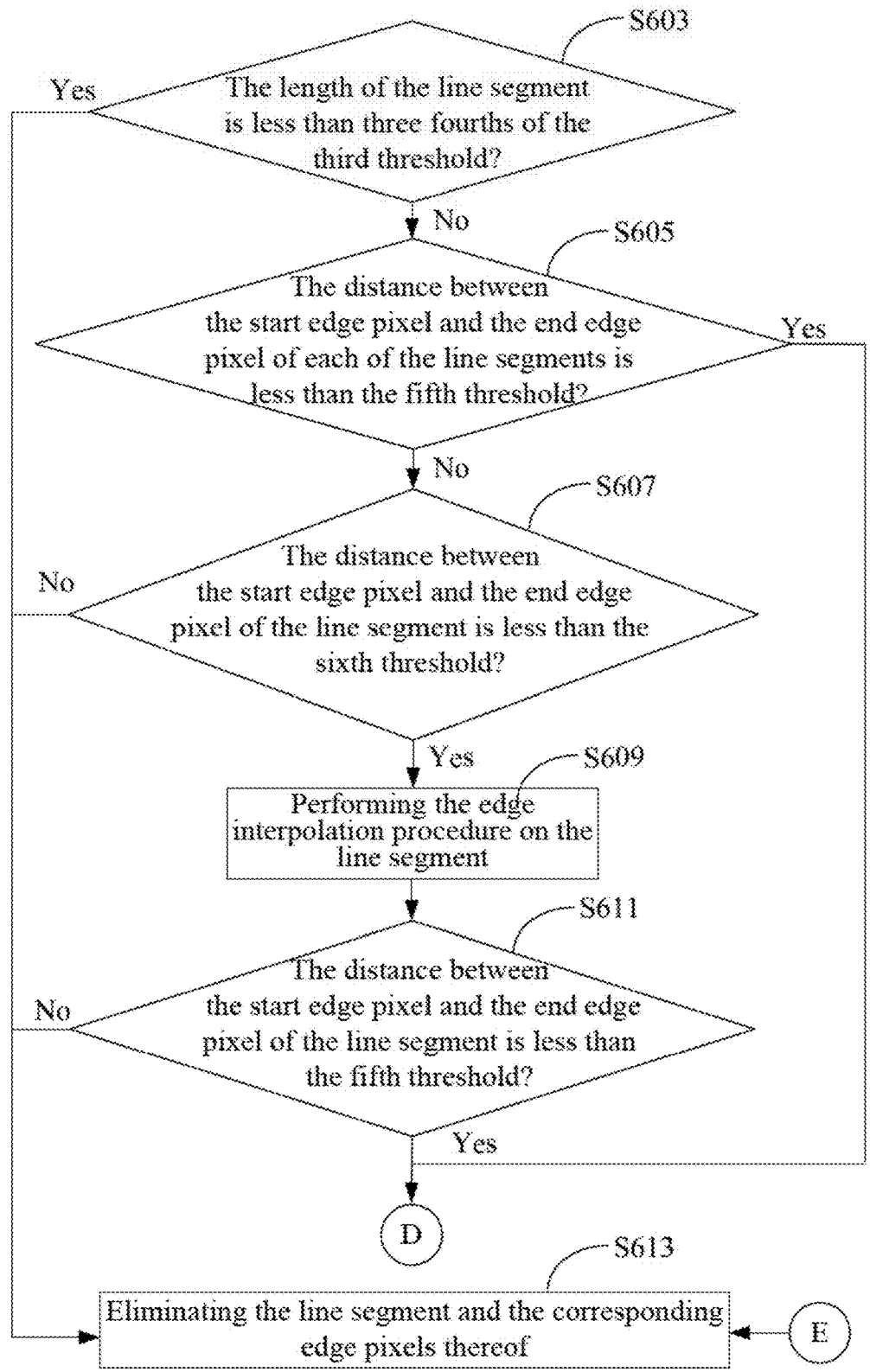
Figure 6C:
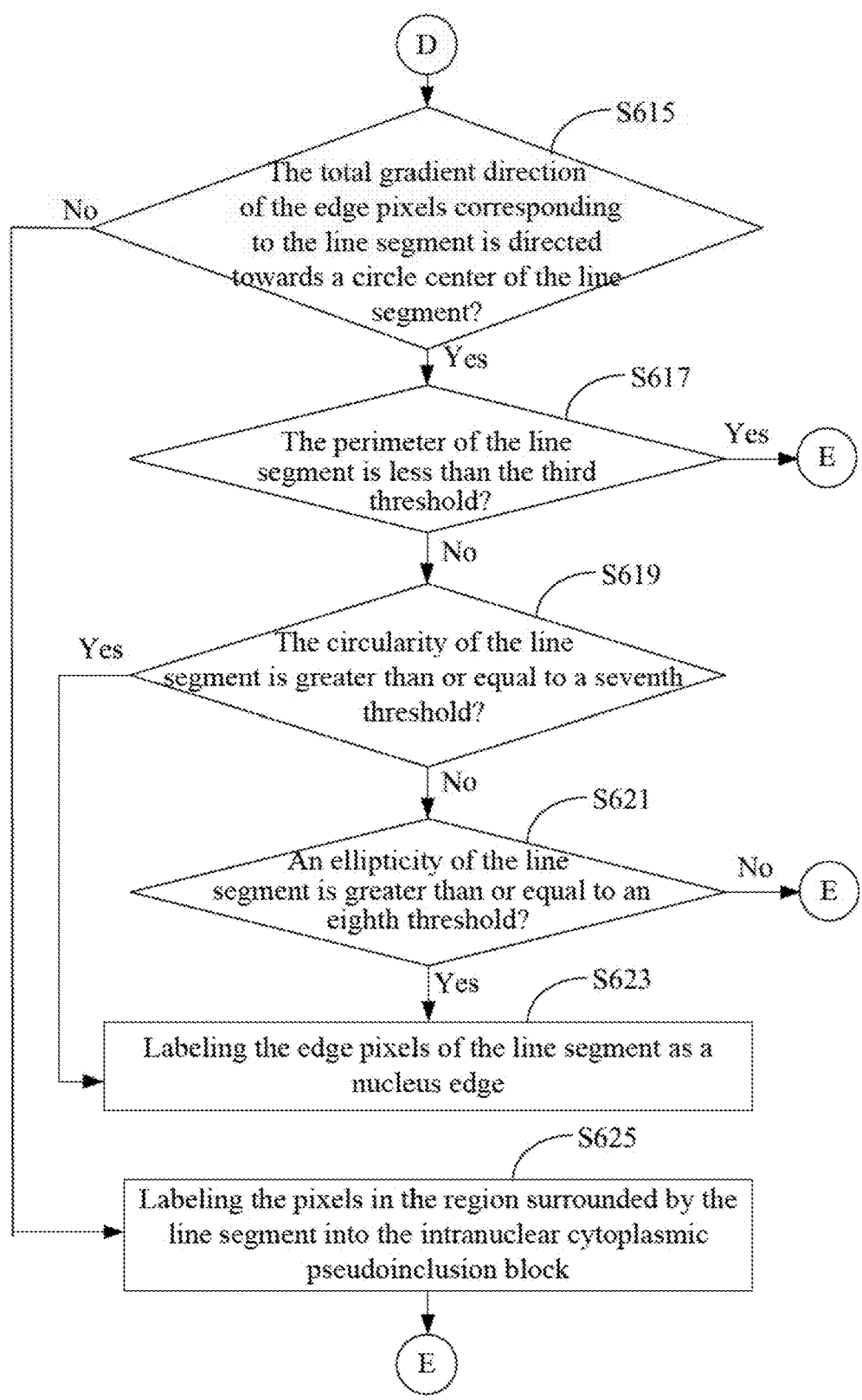

Next, the processor 15 executes the steps as shown in FIG. 6B and FIG. 6C for each of the line segments. In step S603, the processor 15 determines whether the length of the line segment is less than three fourths of the third threshold. If the length of the line segment is less than three fourths of the third threshold, then the processor 15 executes step S613 to eliminate the line segment and the corresponding edge pixels thereof. On the contrary, if the length of the line segment is not less than three fourths of the third threshold, then the processor 15 executes step S605 to determine whether the distance between the start edge pixel and the end edge pixel of each of the line segments is less than the fifth threshold. When the distance is less than the fifth threshold, the processor 15 executes step S615.

On the other hand, when the distance is not less than the fifth threshold, the processor 15 executes step S607 to determine whether the distance between the start edge pixel and the end edge pixel of the line segment is less than the sixth threshold. If the distance is less than the sixth threshold, then the processor 15 executes step S609 to perform the edge interpolation procedure on the line segment. Thereafter, in step S611, the processor 15 determines whether the distance between the start edge pixel and the end edge pixel of the line segment which has been processed by the edge interpolation procedure is less than the fifth threshold. If the distance is not less than the fifth threshold, then the processor 15 executes step S613 to eliminate the line segment and the corresponding edge pixels thereof.

If the distance between the start edge pixel and the end edge pixel of the line segment has become less than the fifth threshold after the edge interpolation procedure, then the processor 15 executes step S615. In the step S615, the processor 15 determines whether the total gradient direction of the edge pixels corresponding to the line segment is directed towards a circle center of a region surrounded by the line segment. If the gradient direction is not directed towards the circle center, then the pixels in the region surrounded by the line segment are labeled into an intranuclear cytoplasmic pseudoinclusion block, and the step S613 is executed to eliminate the line segment and the corresponding edge pixels thereof.

If the gradient direction of the edge pixels corresponding to the line segment is directed towards the circle center of the line segment, then the processor 15 executes step S617 to determine whether the perimeter of the line segment is less than the third threshold. If the perimeter is less than the third threshold, then the step S613 is executed to eliminate the line segment and the corresponding edge pixels thereof. If the perimeter is greater than the third threshold, then the processor 15 executes the step S619. In step S619, the processor 15 determines whether the circularity of the line segment is greater than or equal to a seventh threshold. If the circularity is greater than or equal to the seventh threshold, then the processor 15 executes step S623 to label the edge pixels of the line segment as a nuclear edge, and determine the edge pixels as a complete and nearly round nuclear edge.

On the other hand, if the circularity of the line segment is less than the seventh threshold, then the processor 15 executes step S621 to determine whether an ellipticity of the line segment is greater than or equal to an eighth threshold. If the ellipticity of the line segment is greater than or equal to the eighth threshold, then the step S623 is executed to label the edge pixels of the line segment as a nuclear edge, and determine the edge pixels as a complete and elongated (elliptical) nuclear edge. Subsequently, the elongated nuclear edges are visualized to present at least one elongated nuclear block among the nuclear blocks. On the contrary, if the ellipticity of the line segment is less than the eighth threshold, then the edge pixels of the line segment are determined as irregularly-shaped nuclear edge, and the step S613 is executed to eliminate the line segment and the corresponding edge pixels thereof.

The edge pixels of the line segments which are not eliminated after the above operations are edge pixels of a normal nucleus, so the processor 15 can obtain an edge matrix and connection information of the edge pixels of the edge matrix. In this way, the processor 15 can incorporate the edge matrix obtained based on the temporary background-subtracted images 103_temp and the connection information of the edge matrix into the integrated edge matrix generated in the second embodiment and the integrated connection information of the edge pixels of the integrated edge matrix respectively through the above operations, thereby segmenting the nuclear block 1101 in the background-subtracted image 103 as accurately as possible.

In addition, in the above embodiments, after segmenting the nuclear blocks, for the cytoplasmic part, the processor 15 can further determine whether the cytoplasmic part has a plurality of pixels which are located within the segmented nuclear blocks and are not in the intranuclear cytoplasmic pseudoinclusion blocks, and if such pixels exist, then the processor 15 reclassify these pixels into the nuclear part.

According to the above descriptions, the present invention can provide quantified relevant parameters of the cytological image and analyzed images by dividing the cytological image into a nuclear part and a cytoplasmic part and segmenting nuclear blocks, as compared to the prior art. In this way, the advanced information about the cytological image provided by the present invention can assist the doctor in making the diagnosis for the cytological image, and reduce the disagreement among the diagnosis results made by different doctors for the same cytological image, thereby improving the accuracy of diagnosis when determining the illness condition of the patient.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for quantifying characteristics of cytological image, being used in a cytological image processing device, the method comprising the following steps:
   (a) loading a cytological image having a plurality of pixels;
   (b) removing a background part from the cytological image according to at least one of a plurality of color attributes of each of the pixels in a color space to obtain a background-subtracted image;
   (c) dividing the background-subtracted image into a nuclear part and a cytoplasmic part; and
   (d) generating a nuclei-to-cytoplasm color ratio according to the nuclear part and the cytoplasmic part;
   wherein the step (b) further comprises the following steps:
   (b1) deciding a plurality of first initial reference points according to at least one of the color attributes of the pixels of the cytological image;
   (b2) removing the background part of the cytological image by clustering the pixels of the cytological image according to the first initial reference points to obtain the background-subtracted image;
   (b3) deciding a plurality of second initial reference points according to at least one of the color attributes of the pixels of the background-subtracted image; and
   (b4) removing the background part of the background-subtracted image by clustering the pixels of the background-subtracted image according to the second initial reference points to update the background-subtracted image; and
   wherein the step (c) further comprises the following step:
   (c1) deciding a plurality of third initial reference points according to at least one of the color attributes of the pixels of the background-subtracted image and a weight proportion therebetween, and dividing the background-subtracted image into the nuclear part and the cytoplasmic part by clustering the pixels of the background-subtracted image according to the third initial reference points and the weight proportion.

2. The method according to claim 1, wherein the nuclei-to-cytoplasm color ratio is generated by dividing a function value of the color attributes of the nuclear part by a function value of the color attributes of the cytoplasmic part.

3. A method for quantifying characteristics of cytological image, being used in a cytological image processing device, the method comprising the following steps:
   (a) loading a cytological image having a plurality of pixels;
   (b) removing a background part from the cytological image according to at least one of a plurality of color attributes of each of the pixels in a color space to obtain a background-subtracted image;
   (c) dividing the background-subtracted image into a nuclear part and a cytoplasmic part;
   (d) detecting a plurality of edge pixels in the background-subtracted image to segment a plurality of nuclear blocks in the background-subtracted image;
   (e) generating a parameter set, the parameter set including at least one of the following: a nuclear polarity, an index of intranuclear cytoplasmic pseudoinclusions, and an index of nuclear overlapping and molding, wherein the nuclear polarity is generated according to the nuclear blocks, the index of intranuclear cytoplasmic pseudoinclusions is generated according to the nuclear part, and the index of nuclear overlapping and molding is generated according to the nuclear blocks and the nuclear part; and
   (f) generating an output image by visualizing the background-subtracted image.

4. The method according to claim 3, wherein the step (b) further comprises the following steps:
   (b1) deciding a plurality of first initial reference points according to at least one of the color attributes of the pixels of the cytological image;
   (b2) removing the background part of the cytological image by clustering the pixels of the cytological image according to the first initial reference points to obtain the background-subtracted image;
   (b3) deciding a plurality of second initial reference points according to at least one of the color attributes of the pixels of the background-subtracted image; and
   (b4) removing the background part of the background-subtracted image by clustering the pixels of the background-subtracted image according to the second initial reference points to update the background-subtracted image;
   wherein the step (c) further comprises the following step:
   (c1) deciding a plurality of third initial reference points according to at least one of the color attributes of the pixels of the background-subtracted image and a weight proportion therebetween, and dividing the background-subtracted image into the nuclear part and the cytoplasmic part by clustering the pixels of the background-subtracted image according to the third initial reference points and the weight proportion.

5. The method according to claim 3, wherein the step (d) further comprises the following steps:
   (d1-1) generating a two-dimensional (2D) grayscale matrix according to at least one of the color attributes of the pixels of the background-subtracted image;
   (d1-2) multiplying the 2D grayscale matrix with a Deriche filter matrix having an $i^{th}$ parameter to obtain an $i^{th}$ 2D gradient matrix, the $i^{th}$ 2D gradient matrix recording a horizontal-direction gradient and a vertical-direction gradient of each of the pixels with respect to neighboring pixels of the pixel, where i has an initial value of 1;
   (d1-3) applying a mask to the $i^{th}$ 2D gradient matrix, determining whether a total gradient magnitude of a middle pixel in the mask is a relative maximum value in the mask, and if the total gradient magnitude of the middle pixel in the mask is not the relative maximum value in the mask, then setting the horizontal-direction gradient and the vertical-direction gradient of the middle pixel to be 0 to update the $i^{th}$ 2D gradient matrix; and
   (d1-4) applying the mask to the updated $i^{th}$ 2D gradient matrix, determining whether neither of the total gradient magnitude of a neighboring vertical pixel and the total gradient magnitude of a neighboring horizontal pixel of the middle pixel in the mask is equal to 0, and if neither of the total gradient magnitude of the neighboring vertical pixel and the total gradient magnitude of the neighboring horizontal pixel of the middle pixel in the mask is equal to 0, then setting the horizontal-direction gradient and the vertical-direction gradient of the middle pixel to be 0 to update the $i^{th}$ 2D gradient matrix, wherein the pixels having the total gradient magnitude not equal to 0 in the updated $i^{th}$ 2D gradient matrix are the edge pixels;

(d1-5) setting i to be 2 and executing the aforesaid steps (d1-2) to (d1-4) to obtain a $2^{nd}$ 2D gradient matrix; and (d1-6) setting i to be 3 and executing the aforesaid steps (d1-2) to (d1-4) to obtain a $3^{rd}$ 2D gradient matrix;

wherein for the $i^{th}$ 2D gradient matrix, where i is 1 to 3, the step (d) further comprises the following steps:

(d2-1) connecting the edge pixels according to a 8-connection connectivity rule to form a plurality of line segments, wherein the total gradient magnitude of a next edge pixel connected to a current edge pixel is greater than a first threshold and an angle between a total gradient direction of the current edge pixel and the total gradient direction of the next edge pixel connected to the current edge pixel is less than a second threshold;

(d2-2) eliminating the line segment, a length of which is less than three fourths of a third threshold or an average gradient of which is less than a fourth threshold, and the corresponding edge pixels thereof;

(d2-3) determining whether a distance between a start edge pixel and an end edge pixel of each of the line segments is less than a fifth threshold;

(d2-4) for the line segment, the distance between the start edge pixel and the end edge pixel of which is not less than the fifth threshold, determining whether the distance between the start edge pixel and the end edge pixel of the line segment is less than a sixth threshold, and if the distance is less than the sixth threshold, then performing an edge interpolation procedure on the line segment;

(d2-5) for the line segment which has been processed by the edge interpolation procedure, determining whether the distance between the start edge pixel and the end edge pixel of the line segment is less than the fifth threshold, and eliminating the line segment, the distance of which is not less than the fifth threshold, and the corresponding edge pixels thereof;

(d2-6) for each of the line segments, determining whether the total gradient direction of the edge pixels corresponding to the line segment is directed towards a circle center of a region surrounded by the line segment;

(d2-7) for the line segment, the total gradient direction of the edge pixels of which is not directed towards the circle center, labeling the pixels in the region surrounded by the line segment into an intranuclear cytoplasmic pseudoinclusion block, and eliminating the line segment and the corresponding edge pixels thereof;

(d2-8) for the line segment, the total gradient direction of the edge pixels of which is directed towards the circle center, determining whether a perimeter of the line segment is less than the third threshold, and eliminating the line segment, the perimeter of which is less than the third threshold, and the corresponding edge pixels thereof;

(d2-9) for the line segment, the perimeter of which is not less than the third threshold, determining whether a circularity of the line segment is less than a seventh threshold;

(d2-10) for the line segment, the circularity of which is less than the seventh threshold, determining whether an ellipticity of the line segment is less than an eighth threshold, and eliminating the line segment, the ellipticity of which is less than the eighth threshold, and the corresponding edge pixels thereof; and (d2-11) generating an $i^{th}$ edge matrix and $i^{th}$ connection information of the edge pixels of the $i^{th}$ edge matrix according to the line segments, which are not eliminated, and the corresponding edge pixels thereof;

wherein the step (d) further comprises the following steps:

(d2-12) integrating the $1^{st}$ edge matrix, the $2^{nd}$ edge matrix and the $3^{rd}$ edge matrix as well as the $1^{st}$ connection information, the $2^{nd}$ connection information and the $3^{rd}$ connection information to obtain an integrated edge matrix and integrated connection information of the edge pixels of the integrated edge matrix; and (d2-13) segmenting the nuclear blocks in the background-subtracted image according to the integrated edge matrix and the integrated connection information of the edge pixels of the integrated edge matrix.

6. The method according to claim 5, wherein the step (d) further comprises the following steps:

(d3-1) setting the pixels within a region surrounded by each of the line segments in the background-subtracted image as background pixels according to the $i^{th}$ edge matrix and the $i^{th}$ connection information of the edge pixels of the $i^{th}$ edge matrix to generate a temporary background-subtracted image;

(d3-2) generating a 2D grayscale matrix according to at least one of the color attributes of the pixels of the temporary background-subtracted image, and executing the steps (d1-2) to (d1-4) and the steps (d2-1) to (d2-11) to obtain the $i^{th}$ edge matrix of the temporary background-subtracted image and the $i^{th}$ connection information of the edge pixels of the $i^{th}$ edge matrix;

(d3-3) determining whether there are the edge pixels in the $i^{th}$ edge matrix of the temporary background-subtracted image;

(d3-4) if there are the edge pixels, then incorporating the $i^{th}$ edge matrix of the temporary background-subtracted image and the $i^{th}$ connection information of the edge pixels of the $i^{th}$ edge matrix into the $i^{th}$ edge matrix of the background-subtracted image and the $i^{th}$ connection information of the edge pixels of the $i^{th}$ edge matrix respectively; and (d3-5) repeating the aforesaid steps (d3-1) to (d3-4) until it is determined that there is no edge pixel in the step (d3-3).

7. The method according to claim 5, wherein the step (d) further comprises the following steps:

(d4-1) setting the pixels within the region surrounded by each of the line segments in the background-subtracted image to be the background pixels according to the integrated edge matrix and the connection information of the edge pixels of the integrated edge matrix to generate a temporary background-subtracted image;

(d4-2) generating a 2D binarized matrix according to at least one of the color attributes of the pixels of the temporary background-subtracted image;

(d4-3) multiplying the 2D binarized matrix with a Deriche filter matrix having a parameter to obtain a 2D gradient matrix, the 2D gradient matrix recording the horizontal-direction gradient and the vertical-direction gradient of each of the pixels with respect to neighboring pixels thereof;

(d4-4) applying the mask to the 2D gradient matrix, determining whether the total gradient magnitude of the middle pixel in the mask is a relative maximum value in the mask, and if the total gradient magnitude of the middle pixel in the mask is not the relative maximum value in the mask, then setting the horizontal-direction gradient and the vertical-direction gradient of the middle pixel to be 0 to update the 2D gradient matrix; and (d4-5) applying the mask to the updated 2D gradient matrix, determining whether neither of the total gradient magnitude of the neighboring vertical pixel and the total gradient magnitude of the neighboring horizontal pixel of the middle pixel in the mask is equal to 0, and if neither of the total gradient magnitude of the neighboring vertical pixel and the total gradient magnitude of the neighboring horizontal pixel of the middle pixel is equal to 0, then setting the horizontal-direction gradient and the vertical-direction gradient of the middle pixel to be 0 to update the 2D gradient matrix, wherein the pixels having the total gradient magnitude not equal to 0 in the updated 2D gradient matrix are the edge pixels;

wherein for the 2D gradient matrix, the step (d) further comprises the following steps:

(d5-1) connecting the edge pixels according to the 8-connection connectivity rule to form a plurality of line segments, wherein an angle between the total gradient direction of the current edge pixel and the total gradient direction of the next edge pixel connected to the current edge pixel is less than the second threshold;

(d5-2) eliminating the line segment, the length of which is less than three fourths of the third threshold and the corresponding edge pixels thereof;

(d5-3) determining whether the distance between the start edge pixel and the end edge pixel of each of the line segments is less than the fifth threshold;

(d5-4) for the line segment, the distance between the start edge pixel and the end edge pixel of which is not less than the fifth threshold, determining whether the distance between the start edge pixel and the end edge pixel of the line segment is less than the sixth threshold, and if the distance is less than the sixth threshold, then performing the edge interpolation procedure on the line segment;

(d5-5) for the line segment which has been processed by the edge interpolation procedure, determining whether the distance between the start edge pixel and the end edge pixel of the line segment is less than the fifth threshold, and eliminating the line segment, the distance of which is greater than the fifth threshold, and the corresponding edge pixels thereof;

(d5-6) for each of the line segments, determining whether the total gradient direction of the edge pixels corresponding to the line segment is directed towards a circle center of a region surrounded by the line segment;

(d5-7) for the line segment, the total gradient direction of the edge pixels of which is not directed towards the circle center, labeling the pixels in the region surrounded by the line segment into an intranuclear cytoplasmic pseudoinclusion block and eliminating the line segment and the corresponding edge pixels thereof;

(d5-8) for the line segment, the total gradient direction of the edge pixels of which is directed towards the circle center, determining whether the perimeter of the line segment is less than the third threshold, and eliminating the line segment, the perimeter of which is less than the third threshold, and the corresponding edge pixels thereof;

(d5-9) for the line segment, the perimeter of which is not less than the third threshold, determining whether the circularity of the line segment is less than a seventh threshold;

(d5-10) for the line segment, the circularity of which is less than the seventh threshold, determining whether an ellipticity of the line segment is less than an eighth threshold, and eliminating the line segment, the ellipticity of which is less than the eighth threshold, and the corresponding edge pixels thereof; and (d5-11) generating an edge matrix and connection information of the edge pixels of the edge matrix according to the line segments, which are not eliminated, and the corresponding edge pixels thereof; and (d5-12) incorporating the edge matrix and the connection information of the edge pixels of the edge matrix into the integrated edge matrix and the integrated connection information of the edge pixels of the integrated edge matrix, respectively.

8. The method according to claim 5, wherein the step (c) further comprises the following steps:

for the cytoplasmic part, determining whether the cytoplasmic part has a plurality of pixels which are located within the segmented nuclear blocks and are not in the intranuclear cytoplasmic pseudoinclusion blocks, and if the cytoplasmic part has the pixels which are located within the segmented nuclear blocks and are not in the intranuclear cytoplasmic pseudoinclusion blocks, then redividing the pixels which are located within the segmented nuclear blocks and are not in the intranuclear cytoplasmic pseudoinclusion blocks into the nuclear part.

9. The method according to claim 5, wherein the step (d2-12) further comprises the following steps:

determining whether there is at least one first new line segment among the line segments of the $2^{nd}$ edge matrix and a plurality of barycenter distances between a barycenter of the at least one first new line segment and a plurality of barycenters of the regions surround by the line segments of the $1^{st}$ edge matrix are all greater than a nuclear average minor-axis length;

if the at least one first new line segment exists, then adding the edge pixels of the at least one first new line segment into the $1^{st}$ edge matrix to generate the integrated edge matrix, and adding connection information associated with the at least one first new line segment into the $1^{st}$ connection information to generate the integrated connection information;

determining whether there is at least one second new line segment among the line segments of the $3^{rd}$ edge matrix, and a plurality of barycenter distances between a barycenter of the at least one second new line segments and a plurality of barycenters of the regions surrounded by the line segments of the integrated edge matrix are all greater than the nuclear average minor-axis length;

if the at least one second new line segment exists, then adding the edge pixels of the at least one second new line segment into the integrated edge matrix to update the integrated edge matrix, and adding connection information associated with the at least one second new line segment into the integrated connection information to update the integrated connection information.

10. The method according to claim 5, wherein the edge interpolation procedure comprises the following step:
adding a plurality of edge pixels gradually from the start edge pixel towards the end edge pixel one by one according to a slope, a horizontal distance and a vertical distance between the start edge pixel and the end edge pixel of the line segment.

11. The method according to claim 3, wherein the output image is used to visualize at least one of a nuclei-to-cytoplasm ratio (NCR), the nuclear blocks, at least one elongated nuclear block among the nuclear blocks, an overlapped nuclear part in the nuclear part, at least one of the intranuclear cytoplasmic pseudoinclusion block, and a nuclear major-axis distribution.

12. The method according to claim 3, wherein the nuclear polarity is generated by calculating a standard deviation of an angle between a nuclear major axis of the segmented nuclear blocks and a horizontal line;
wherein the index of intranuclear cytoplasmic pseudoinclusions is generated by dividing a total area of a plurality of intranuclear cytoplasmic pseudoinclusion blocks in the nuclear part by a total area of the nuclear part; and
wherein the index of nuclear overlapping and molding is generated by dividing a remaining area not belonging to the nuclear blocks in the nuclear part by the total area of the nuclear part.

13. A cytological image processing device, comprising:
a storage, being configured to store a cytological image having a plurality of pixels;
a processor electrically connected to the storage, being configured to execute a method for quantifying characteristics of cytological image, the method comprising the following steps:
(a) loading the cytological image from the storage;
(b) removing a background part from the cytological image according to at least one of a plurality of color attributes of each of the pixels in a color space to obtain a background-subtracted image;
(c) dividing the background-subtracted image into a nuclear part and a cytoplasmic part;
(d) detecting a plurality of edge pixels in the background-subtracted image to segment a plurality of nuclear blocks in the background-subtracted image;
(e) generating a parameter set, the parameter set including at least one of the following: a nuclear polarity, an index of intranuclear cytoplasmic pseudoinclusions, a nuclei-to-cytoplasm color ratio and an index of nuclear overlapping and molding, wherein the nuclei-to-cytoplasm color ratio is generated according to the nuclear part and the cytoplasmic part, the nuclear polarity is generated according to the nuclear blocks, the index of intranuclear cytoplasmic pseudoinclusions is generated according to the nuclear part, and the index of nuclear overlapping and molding is generated according to the nuclear blocks and the nuclear part; and
(f) generating an output image by visualizing the background-subtracted image;
wherein the step (b) further comprises the following steps:
(b1) deciding a plurality of first initial reference points according to at least one of the color attributes of the pixels of the cytological image;
(b2) removing the background part of the cytological image by clustering the pixels of the cytological image according to the first initial reference points to obtain the background-subtracted image;
(b3) deciding a plurality of second initial reference points according to at least one of the color attributes of the pixels of the background-subtracted image; and
(b4) removing the background part of the background-subtracted image by clustering the pixels of the background-subtracted image according to the second initial reference points to update the background-subtracted image;
and wherein the step (c) further comprises the following step:
(c1) deciding a plurality of third initial reference points according to at least one of the color attributes of the pixels of the background-subtracted image and a weight proportion therebetween, and dividing the background-subtracted image into the nuclear part and the cytoplasmic part by clustering the pixels of the background-subtracted image according to the third initial reference points and the weight proportion.

14. The cytological image processing device according to claim 13, further comprising an input interface and an output interface, wherein the processor further loads the cytological image via the input interface and stores the cytological image in the storage, and the processor transmits the output image via the output interface.

15. The cytological image processing device according to claim 13, wherein the step (d) further comprises the following steps:
(d1-1) generating a 2D grayscale matrix according to at least one of the color attributes of the pixels of the background-subtracted image;
(d1-2) multiplying the 2D grayscale matrix with a Deriche filter matrix having an $i^{th}$ parameter to obtain an $i^{th}$ 2D gradient matrix, the $i^{th}$ 2D gradient matrix recording a horizontal-direction gradient and a vertical-direction gradient of each of the pixels with respect to neighboring pixels of the pixel, where i has an initial value of 1;
(d1-3) applying a mask to the $i^{th}$ 2D gradient matrix, determining whether a total gradient magnitude of a middle pixel in the mask is a relative maximum value in the mask, and if the total gradient magnitude of the middle pixel in the mask is not the relative maximum value in the mask, then setting the horizontal-direction gradient and the vertical-direction gradient of the middle pixel to be 0 to update the $i^{th}$ 2D gradient matrix; and
(d1-4) applying the mask to the updated $i^{th}$ 2D gradient matrix, determining whether neither of the total gradient magnitude of a neighboring vertical pixel and the total gradient magnitude of a neighboring horizontal pixel of the middle pixel in the mask is equal to 0, and if neither of the total gradient magnitude of the neighboring vertical pixel and the total gradient magnitude of the neighboring horizontal pixel of the middle pixel in the mask is equal to 0, then setting the horizontal-direction gradient and the vertical-direction gradient of the middle pixel to be 0 to update the $i^{th}$ 2D gradient matrix, wherein the pixels having the total gradient magnitude not equal to 0 in the updated $i^{th}$ 2D gradient matrix are the edge pixels;
(d1-5) setting i to be 2 and executing the aforesaid steps (d1-2) to (d1-4) to obtain a $2^{nd}$ 2D gradient matrix; and
(d1-6) setting i to be 3 and executing the aforesaid steps (d1-2) to (d1-4) to obtain a $3^1$ 2D gradient matrix;
wherein for the $i^{th}$ 2D gradient matrix, where i is 1 to 3, the step (d) further comprises the following steps:

(d2-1) connecting the edge pixels according to a 8-connection connectivity rule to form a plurality of line segments, wherein the total gradient magnitude of a next edge pixel connected to a current edge pixel is greater than a first threshold and an angle between a total gradient direction of the current edge pixel and the total gradient direction of the next edge pixel connected to the current edge pixel is less than a second threshold;

(d2-2) eliminating the line segment, a length of which is less than three fourths of a third threshold or an average gradient of which is less than a fourth threshold, and the corresponding edge pixels thereof;

(d2-3) determining whether a distance between a start edge pixel and an end edge pixel of each of the line segments is less than a fifth threshold;

(d2-4) for the line segment, the distance between the start edge pixel and the end edge pixel of which is not less than the fifth threshold, determining whether the distance between the start edge pixel and the end edge pixel of the line segment is less than a sixth threshold, and if the distance is less than the sixth threshold, then performing an edge interpolation procedure on the line segment;

(d2-5) for the line segment which has been processed by the edge interpolation procedure, determining whether the distance between the start edge pixel and the end edge pixel of the line segment is less than the fifth threshold, and eliminating the line segment, the distance of which is not less than the fifth threshold, and the corresponding edge pixels thereof;

(d2-6) for each of the line segments, determining whether the total gradient direction of the edge pixels corresponding to the line segment is directed towards a circle center of a region surrounded by the line segment;

(d2-7) for the line segment, the total gradient direction of the edge pixels of which is not directed towards the circle center, labeling the pixels in the region surrounded by the line segment into an intranuclear cytoplasmic pseudoinclusion block and eliminating the line segment and the corresponding edge pixels thereof;

(d2-8) for the line segment, the total gradient direction of the edge pixels of which is directed towards the circle center, determining whether a perimeter of the line segment is less than the third threshold, and eliminating the line segment, the perimeter of which is less than the third threshold, and the corresponding edge pixels thereof;

(d2-9) for the line segment, the perimeter of which is not less than the third threshold, determining whether a circularity of the line segment is less than a seventh threshold;

(d2-10) for the line segment, the circularity of which is less than the seventh threshold, determining whether an ellipticity of the line segment is less than an eighth threshold, and eliminating the line segment, the ellipticity of which is less than the eighth threshold, and the corresponding edge pixels thereof; and (d2-11) generating an $i^{th}$ edge matrix and $i^{th}$ connection information of the edge pixels of the $i^{th}$ edge matrix according to the line segments, which are not eliminated, and the corresponding edge pixels thereof;

wherein the step (d) further comprises the following steps:

(d2-12) integrating the $1^{st}$ edge matrix, the $2^{nd}$ edge matrix and the $3^{rd}$ edge matrix as well as the $1^{st}$ connection information, the $2^{nd}$ connection information and the $3^{rd}$ connection information to obtain an integrated edge matrix and integrated connection information of the edge pixels of the integrated edge matrix; and (d2-13) segmenting the nuclear blocks in the background-subtracted image according to the integrated edge matrix and the integrated connection information of the edge pixels of the integrated edge matrix.

* * * * *